US011426373B2

(12) United States Patent
Allphin et al.

(10) Patent No.: US 11,426,373 B2
(45) Date of Patent: Aug. 30, 2022

(54) GAMMA-HYDROXYBUTYRATE COMPOSITIONS AND THEIR USE FOR THE TREATMENT OF DISORDERS

(71) Applicant: Jazz Pharmaceuticals Ireland Limited, Dublin (IE)

(72) Inventors: Clark P. Allphin, Seattle, WA (US); Gunjan Junnarkar, Palo Alto, CA (US); Roman Skowronski, Palo Alto, CA (US); Cuiping Chen, Palo Alto, CA (US); Katayoun Zomorodi, San Jose, CA (US); Mark Eller, Redwood City, CA (US)

(73) Assignee: Jazz Pharmaceuticals Ireland Limited, Dublin (IE)

( * ) Notice: Subject to any disclaimer, the term of this patent is extended or adjusted under 35 U.S.C. 154(b) by 0 days.

(21) Appl. No.: 17/131,418

(22) Filed: Dec. 22, 2020

(65) Prior Publication Data

US 2021/0121423 A1 Apr. 29, 2021

Related U.S. Application Data

(63) Continuation of application No. 16/575,213, filed on Sep. 18, 2019, now abandoned, which is a continuation of application No. 15/709,262, filed on Sep. 19, 2017, now abandoned.

(60) Provisional application No. 62/473,232, filed on Mar. 17, 2017.

(51) Int. Cl.
*A61K 31/19* (2006.01)
*A61P 25/20* (2006.01)

(52) U.S. Cl.
CPC .......... *A61K 31/19* (2013.01); *A61K 2300/00* (2013.01)

(58) Field of Classification Search
CPC ................................. A61K 31/19; A61P 25/20
See application file for complete search history.

(56) References Cited

U.S. PATENT DOCUMENTS

| | | |
|---|---|---|
| 3,051,619 A | 8/1962 | Laborit |
| 3,419,588 A | 12/1968 | De Man |
| 4,221,778 A | 9/1980 | Raghunathan |
| 4,374,441 A | 2/1983 | Carter et al. |
| 4,393,236 A | 7/1983 | Klosa |
| 4,510,128 A | 4/1985 | Khanna |
| 4,524,217 A | 6/1985 | Davenport et al. |
| 4,687,662 A | 8/1987 | Schobel |
| 4,738,985 A | 4/1988 | Kluger et al. |
| 4,916,161 A | 4/1990 | Patell |
| 4,939,949 A | 7/1990 | Langenberg |
| 4,983,632 A | 1/1991 | Gessa et al. |
| 5,294,430 A | 3/1994 | Borch et al. |
| 5,380,937 A | 1/1995 | Koehler et al. |
| 5,415,870 A | 5/1995 | Gergely et al. |
| 5,594,030 A | 1/1997 | Conte et al. |
| 5,753,708 A | 5/1998 | Koehler et al. |
| 5,758,095 A | 5/1998 | Albaum et al. |
| 5,833,599 A | 11/1998 | Schrier et al. |
| 5,840,331 A | 11/1998 | Van Cauter et al. |
| 5,845,255 A | 12/1998 | Mayuad |
| 5,955,106 A | 9/1999 | Moeckel et al. |
| 5,990,162 A | 11/1999 | Sharf |
| 6,014,631 A | 1/2000 | Teagarden et al. |
| 6,022,562 A | 2/2000 | Autant et al. |
| 6,067,524 A | 5/2000 | Byerly et al. |
| 6,112,182 A | 8/2000 | Akers et al. |
| 6,317,719 B1 | 11/2001 | Schrier et al. |
| 6,322,819 B1 | 11/2001 | Burnside et al. |
| 6,356,873 B1 | 3/2002 | Teagarden et al. |
| 6,384,020 B1 | 5/2002 | Flanner et al. |
| 6,436,998 B1 | 8/2002 | Cacciaglia et al. |
| 6,472,431 B2 | 10/2002 | Cook et al. |
| 6,472,432 B1 | 10/2002 | Perricone |
| 6,495,598 B1 | 12/2002 | Yoneda et al. |
| 6,565,872 B2 | 5/2003 | Wu et al. |
| 6,780,889 B2 | 8/2004 | Cook et al. |
| 7,015,200 B2 | 3/2006 | Mamelak et al. |
| 7,072,840 B1 | 7/2006 | Mayuad |
| 7,262,219 B2 | 8/2007 | Cook et al. |
| 7,568,822 B2 | 8/2009 | Ibrahim |
| 7,668,730 B2 | 2/2010 | Reardan et al. |

(Continued)

FOREIGN PATENT DOCUMENTS

| | | |
|---|---|---|
| CA | 2 112663 C | 4/2002 |
| CA | 2 510 289 A1 | 7/2004 |

(Continued)

OTHER PUBLICATIONS

"Guidance for Industry. Food-Effect Bioavailability and Fed Bioequivalence Studies." U.S. Department of Health and Human Services Food and Drug Administration Center for Drug Evaluation and Research (CDER). Dec. 2002. (Year: 2002).*
Borgen et al. (The Influence of Gender and Food on the Pharmacokinetics of Sodium Oxybate Oral Solution in Healthy Subjects. Journal of Clinical Pharmacology, 2003;43:59-65). (Year: 2003).*
"HIB-IMUNE," Physicians Desk Reference (41st ed.), (1987), 1095-1096.
"HibVAX," Physicians Desk Reference (41st ed.), (1987), 870.
"Phospholine Iodide," Physicians Desk Reference (50th ed.), (1996), 2784.
"Taxotere," Physicians Desk Reference (51st ed.), (1997), 2204-2207.

(Continued)

*Primary Examiner* — Jeffrey S Lundgren
*Assistant Examiner* — Chris E Simmons
(74) *Attorney, Agent, or Firm* — Cooley LLP

(57) ABSTRACT

Provided herein are pharmaceutical compositions and formulations comprising mixed salts of gamma-hydroxybutyrate (GHB). Also provided herein are methods of making the pharmaceutical compositions and formulations, and methods of their use for the treatment of sleep disorders such as apnea, sleep time disturbances, narcolepsy, cataplexy, sleep paralysis, hypnagogic hallucination, sleep arousal, insomnia, and nocturnal myoclonus.

11 Claims, 6 Drawing Sheets

(56) References Cited

U.S. PATENT DOCUMENTS

Figure 1:
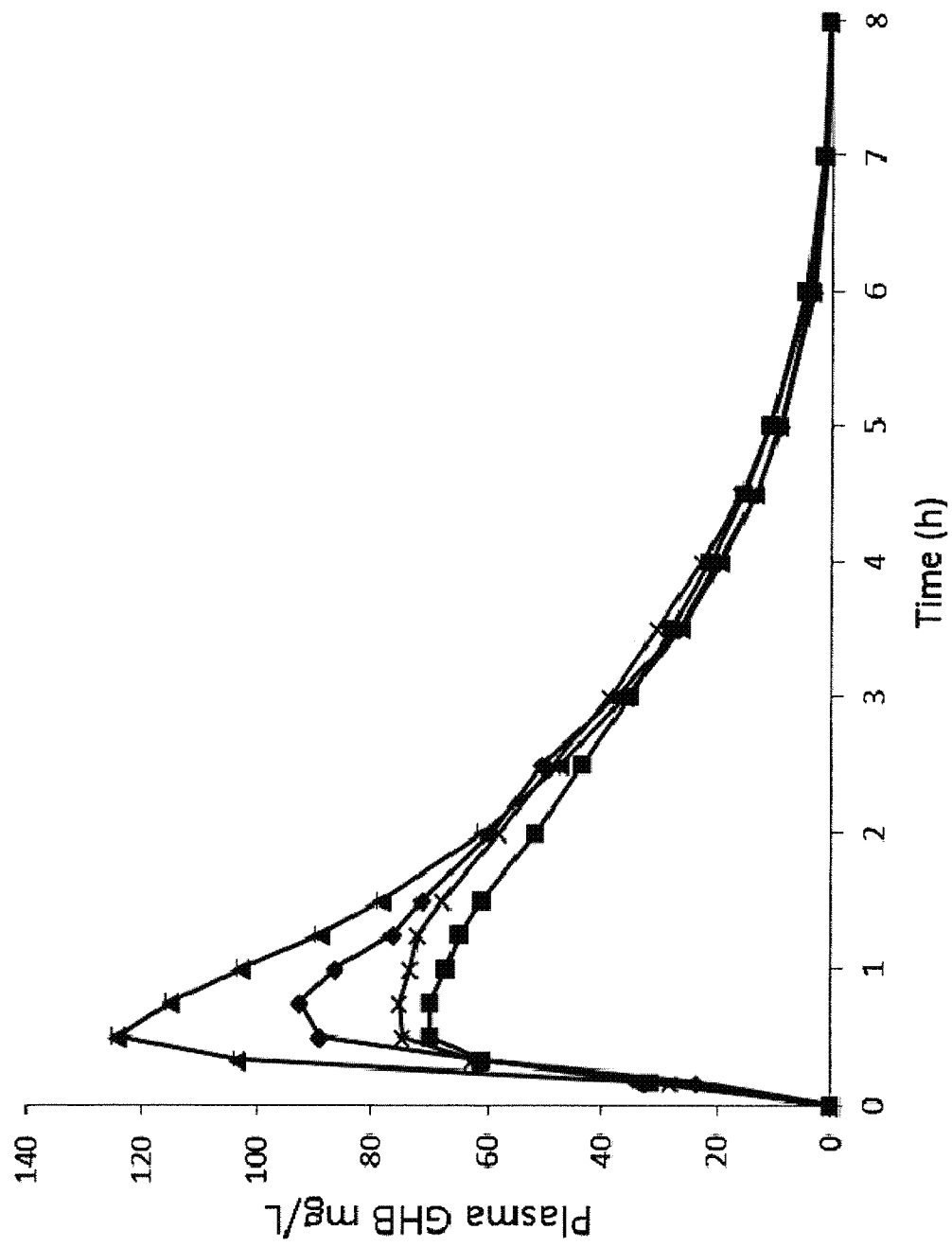

| | | |
|---|---|---|
| 7,765,106 B2 | 7/2010 | Reardan et al. |
| 7,765,107 B2 | 7/2010 | Reardan et al. |
| 7,797,171 B2 | 9/2010 | Reardan et al. |
| 7,851,506 B2 | 12/2010 | Cook et al. |
| 7,895,059 B2 | 2/2011 | Reardan et al. |
| 8,101,209 B2 | 1/2012 | Legrand et al. |
| 8,193,211 B2 | 6/2012 | Liang et al. |
| 8,202,537 B2 | 6/2012 | Mehta et al. |
| 8,263,125 B2 | 9/2012 | Vaya et al. |
| 8,263,650 B2 | 9/2012 | Cook et al. |
| 8,324,275 B2 | 12/2012 | Cook et al. |
| 8,457,988 B1 | 6/2013 | Reardan et al. |
| 8,461,197 B2 | 6/2013 | Tung |
| 8,461,203 B2 | 6/2013 | Cook et al. |
| 8,529,954 B2 | 9/2013 | Lebon et al. |
| 8,589,182 B1 | 11/2013 | Reardan et al. |
| 8,591,922 B1 | 11/2013 | Allphin et al. |
| 8,598,191 B2 | 12/2013 | Liang et al. |
| 8,680,228 B2 | 3/2014 | Guo et al. |
| 8,731,963 B1 | 5/2014 | Reardan et al. |
| 8,759,394 B2 | 6/2014 | Tung et al. |
| 8,771,735 B2 | 7/2014 | Rourke et al. |
| 8,772,306 B1 | 7/2014 | Eller |
| 8,778,301 B2 | 7/2014 | Mamelak et al. |
| 8,778,398 B2 | 7/2014 | Rourke et al. |
| 8,859,619 B2 | 10/2014 | Cook et al. |
| 8,901,173 B2 | 12/2014 | Allphin et al. |
| 8,952,029 B2 | 2/2015 | Eller |
| 8,952,062 B2 | 2/2015 | Cook et al. |
| 9,023,400 B2 | 5/2015 | Guimberteau et al. |
| 9,050,302 B2 | 9/2015 | Eller |
| 9,132,107 B2 | 9/2015 | Allphin et al. |
| 9,486,426 B2 | 11/2016 | Eller |
| 9,539,330 B2 | 1/2017 | Cook et al. |
| 9,555,017 B2 | 1/2017 | Allphin et al. |
| 9,770,514 B2 | 9/2017 | Ghebre-Sellassie |
| 9,795,567 B2 | 10/2017 | Rourke et al. |
| 9,801,852 B2 | 10/2017 | Allphin |
| 10,195,168 B2 | 2/2019 | Allphin et al. |
| 10,213,400 B2 | 2/2019 | Eller |
| 10,272,062 B2 | 4/2019 | Mégret et al. |
| 10,398,662 B1 | 9/2019 | Allphin et al. |
| 10,736,866 B2 | 8/2020 | Mégret et al. |
| 10,758,488 B2 | 9/2020 | Allphin et al. |
| 10,813,885 B1 | 10/2020 | Allphin et al. |
| 10,925,844 B2 | 2/2021 | Grassot et al. |
| 10,952,986 B2 | 3/2021 | Megret et al. |
| 10,959,956 B2 | 3/2021 | Allphin et al. |
| 10,966,931 B2 | 4/2021 | Allphin et al. |
| 10,973,795 B2 | 4/2021 | Megret et al. |
| 10,987,310 B2 | 4/2021 | Allphin et al. |
| 11,077,079 B1 | 8/2021 | Allphin et al. |
| 11,090,269 B1 | 8/2021 | Allphin et al. |
| 2003/0180249 A1 | 9/2003 | Khanna et al. |
| 2004/0092455 A1 | 5/2004 | Mamelak et al. |
| 2005/0031688 A1 | 2/2005 | Ayala |
| 2005/0037077 A1 | 2/2005 | Legrand et al. |
| 2005/0113366 A1 | 5/2005 | Bourguignon et al. |
| 2005/0142192 A1 | 6/2005 | Benjamin et al. |
| 2006/0018933 A1 | 1/2006 | Vaya et al. |
| 2006/0024365 A1 | 2/2006 | Vaya et al. |
| 2006/0069040 A1 | 3/2006 | Mamelak |
| 2006/0210630 A1 | 9/2006 | Liang et al. |
| 2006/0228410 A1 | 10/2006 | Dumont et al. |
| 2007/0270491 A1 | 11/2007 | Cook et al. |
| 2008/0003267 A1 | 1/2008 | Spencer et al. |
| 2008/0069871 A1 | 3/2008 | Vaughn et al. |
| 2008/0085304 A1 | 4/2008 | Baichwal et al. |
| 2008/0118571 A1 | 5/2008 | Lee et al. |
| 2008/0226564 A1 | 9/2008 | Weers et al. |
| 2008/0292700 A1 | 11/2008 | Nghiem et al. |
| 2008/0293698 A1 | 11/2008 | Johnson |
| 2009/0137565 A1 | 5/2009 | Frucht |
| 2009/0155357 A1 | 6/2009 | Muhuri |
| 2009/0317355 A1 | 12/2009 | Roth et al. |
| 2010/0112056 A1 | 5/2010 | Rourke et al. |
| 2010/0266701 A1 | 10/2010 | Guimberteau et al. |
| 2011/0034727 A1 | 2/2011 | Luchi et al. |
| 2011/0039929 A1 | 2/2011 | Cook et al. |
| 2011/0091537 A1 | 4/2011 | Castan et al. |
| 2011/0111027 A1 | 5/2011 | Rourke et al. |
| 2011/0213004 A1 | 9/2011 | Kim et al. |
| 2012/0020833 A1 | 1/2012 | Cook et al. |
| 2012/0076865 A1 | 3/2012 | Allphin et al. |
| 2012/0148672 A1 | 6/2012 | Mehta et al. |
| 2012/0202879 A1 | 8/2012 | Cook et al. |
| 2012/0202880 A1 | 8/2012 | Cook et al. |
| 2013/0230587 A1 | 9/2013 | Pilgaonkar et al. |
| 2013/0273159 A1 | 10/2013 | Howard et al. |
| 2014/0004202 A1 | 1/2014 | Suplie et al. |
| 2014/0037745 A1 | 2/2014 | Liang et al. |
| 2014/0072624 A1 | 3/2014 | Jung et al. |
| 2014/0093578 A1 | 4/2014 | Mehta et al. |
| 2014/0127306 A1 | 5/2014 | Mehta et al. |
| 2014/0141090 A1 | 5/2014 | Wilson |
| 2014/0171506 A1 | 6/2014 | Allphin et al. |
| 2014/0271896 A1 | 9/2014 | Abu Shmeis et al. |
| 2014/0348917 A1 | 11/2014 | Rourke et al. |
| 2015/0005334 A1 | 1/2015 | Shah et al. |
| 2015/0073052 A1 | 3/2015 | Cook et al. |
| 2015/0328168 A1 | 11/2015 | Daviaud-Venet et al. |
| 2016/0068463 A1 | 3/2016 | Peoples et al. |
| 2016/0228379 A1 | 8/2016 | Kumar et al. |
| 2016/0271070 A1 | 9/2016 | Singh et al. |
| 2016/0338966 A1 | 11/2016 | Guimberteau et al. |
| 2016/0346200 A1 | 12/2016 | Sommer et al. |
| 2016/0346216 A1 | 12/2016 | Chen |
| 2017/0119627 A1 | 5/2017 | Bhargava et al. |
| 2017/0340519 A9 | 11/2017 | Bhargava et al. |
| 2018/0008539 A1 | 1/2018 | Singh et al. |
| 2018/0021284 A1 | 1/2018 | Mégret et al. |
| 2018/0042855 A1 | 2/2018 | Rourke et al. |
| 2018/0263936 A1 | 9/2018 | Allphin et al. |
| 2018/0318222 A1 | 11/2018 | Allphin et al. |
| 2019/0183806 A1 | 6/2019 | Guillard |
| 2019/0183836 A1 | 6/2019 | Mégret et al. |
| 2019/0269640 A1 | 9/2019 | Mégret et al. |
| 2019/0269641 A1 | 9/2019 | Mégret et al. |
| 2019/0274990 A1 | 9/2019 | Mégret et al. |
| 2019/0282532 A1 | 9/2019 | Mégret et al. |
| 2020/0113840 A1 | 4/2020 | Allphin et al. |
| 2020/0197347 A1 | 6/2020 | Mégret et al. |
| 2020/0276142 A1 | 9/2020 | Grassot et al. |
| 2020/0330393 A1 | 10/2020 | Walsh et al. |
| 2020/0360293 A1 | 11/2020 | Guillard |
| 2020/0360319 A1 | 11/2020 | Grassot et al. |
| 2020/0368187 A1 | 11/2020 | Grassot et al. |
| 2021/0186907 A1 | 6/2021 | Skobieranda |

FOREIGN PATENT DOCUMENTS

| | | |
|---|---|---|
| CN | 102905688 A | 1/2013 |
| CN | 102958930 A | 3/2013 |
| CN | 103209966 A | 7/2013 |
| CN | 103209967 A | 7/2013 |
| EP | 0203768 A2 | 12/1986 |
| EP | 0235408 A1 | 9/1987 |
| EP | 0344704 A1 | 6/1989 |
| EP | 0635265 A1 | 7/1994 |
| EP | 0616804 A1 | 9/1994 |
| EP | 0635265 A1 | 1/1995 |
| EP | 0709087 B1 | 12/1999 |
| EP | 1140061 A2 | 10/2001 |
| EP | 1140061 B1 | 10/2001 |
| EP | 1316309 A1 | 6/2003 |
| EP | 2760911 B1 | 11/2017 |
| EP | 1434572 B1 | 12/2017 |
| GB | 922029 | 3/1963 |
| GB | 2295390 A | 5/1996 |
| JP | 57-042651 | 3/1982 |
| JP | 62-12715 A | 1/1987 |
| JP | 04-049212 | 2/1992 |
| JP | 05-508422 | 11/1993 |
| JP | H06-508839 A | 10/1994 |

(56) References Cited

FOREIGN PATENT DOCUMENTS

| | | |
|---|---|---|
| JP | 7-53365 A | 2/1995 |
| JP | H8-511257 A | 11/1996 |
| JP | 09-104620 A | 4/1997 |
| JP | H10-505604 A | 6/1998 |
| JP | 2001-513552 A | 9/2001 |
| JP | 2002533388 A | 10/2002 |
| JP | 2004-514732 A | 5/2004 |
| JP | 2007-521231 A | 8/2007 |
| JP | 2008-512386 A | 4/2008 |
| JP | 2008-519847 A | 6/2008 |
| JP | 2008-528571 A | 7/2008 |
| JP | 2009-532331 A | 9/2009 |
| JP | 2011-500865 A | 1/2011 |
| JP | 2012507532 A | 3/2012 |
| RU | 2210360 C1 | 8/2003 |
| WO | WO 1994/028880 A1 | 12/1994 |
| WO | WO 9640105 A1 | 12/1996 |
| WO | WO 1999/009972 A1 | 3/1999 |
| WO | WO 0038672 A2 | 7/2000 |
| WO | WO 2002/045684 A2 | 6/2002 |
| WO | WO 2005/016318 A1 | 2/2005 |
| WO | WO 2005/099671 A2 | 10/2005 |
| WO | WO 2006/029155 A2 | 3/2006 |
| WO | WO 2006/053186 A2 | 5/2006 |
| WO | WO 2006/080029 A1 | 8/2006 |
| WO | WO 2007/053698 A2 | 5/2007 |
| WO | WO 2007/103200 A2 | 9/2007 |
| WO | WO 2008/086804 A2 | 7/2008 |
| WO | WO 2009/056550 A2 | 5/2009 |
| WO | WO 2010/055260 A1 | 5/2010 |
| WO | WO 2010053691 A1 | 5/2010 |
| WO | WO 2011/119839 A1 | 9/2011 |
| WO | WO 2011/127252 A2 | 10/2011 |
| WO | WO 2011/135461 A2 | 11/2011 |
| WO | WO 2011/140310 A2 | 11/2011 |
| WO | WO 2011139271 A1 | 11/2011 |
| WO | WO 2012/028688 A1 | 3/2012 |
| WO | WO 2012/107652 A1 | 8/2012 |
| WO | WO 2014/078014 A2 | 5/2014 |
| WO | WO 2014/093791 A1 * | 6/2014 |
| WO | WO 2015/120006 A1 | 8/2015 |
| WO | WO 2015/120110 A2 | 8/2015 |
| WO | WO 2015/166473 A1 | 11/2015 |
| WO | WO 2016/087952 A1 | 6/2016 |
| WO | WO 2016/178132 A1 | 10/2016 |
| WO | WO 2017/147375 A1 | 8/2017 |
| WO | WO 2017/182851 A1 | 10/2017 |
| WO | WO 2018/015563 A1 | 1/2018 |
| WO | WO 2019/123269 A1 | 6/2019 |
| WO | WO 2020/178695 A1 | 9/2020 |

OTHER PUBLICATIONS

21 C.F.R. 184, Food and Drug Administration, HHS, (1998), pp. 441-535.
Activase, Physicians Desk Reference (50th ed.), (1996), pp. 312,1058-1061.
Akifuddin et al. "Preparation, characterization and in-vitro evaluation of microcapsules for controlled release of Diltiazem hydrochloride by Ionotropic gelation technique." Journal of Applied Pharmaceutical Science (2013); 3.4: 35-42.
Alshaikh et al., "Sodium Oxybate for Narcolepsy with Cataplexy: Systematic Review and Meta-Analysis," Journal of Clinical Sleep Medicine, 2012, vol. 8, No. 4, 451-458.
Anand et al. "Ion-exchange resins: carrying drug delivery forward." Drug Discovery Today (2001); 6.17: 905-914.
Baldrick, P., "Pharmaceutical Excipient Development: The Need for Preclinical Guidance," Regul. Toxicol. Pharmacol. Oct. 2000 32(2):210-218.
Bodmeier, R., "Tableting of coated pellets," European Journal of Pharmaceutics and Biopharmaceutics, (1997) 43(1), 1-8.
Borgen et al., "The influence of gender and food on the pharmacokinetics of sodium oxybate oral solution in healthy subjects." J Clin Pharmacol. (2003); 43(1): 59-65.
Borgen, L., et al. "Xyrem® (sodium oxybate): A Study of Dose Proportionality in Healthy Human Subjects." J. Clin. Pharmacol. (2000); 40:1053.
Broughton, et al. "Effects of Nocturnal Gamma-Hydroxybutyrate on Spell/Waking Patterns in Narcolepsy-Cataplexy." Can J. Neural Sci (1980); 7 (1): 23-31.
Broughton, et al. "Gamma-Hydroxy-Butyrate in the Treatment of Narcolepsy: a Preliminary Report." (1976) Narcolepsy, Ny, N.Y., Spectrum Publications, Inc. 659-668.
Caballero et al. "Characterization of alginate beads loaded with ibuprofen lysine salt and optimization of the preparation method." International Journal of Pharmaceutics (2014); 460.1: 181-188.
Chern Abstract ES302338, SciFinder®, (1964), 1 pg.
Chemical Abstracts: Seventh Collective Index, vols. 56-65, (1962-1966), 4 pgs.
Davis et al. "Active chloride secretion in the normal human jejunum." J Clin Invest. (1980); 66(6): 1326-1333.
Frucht, et al. "A pilot Tolerability and Efficacy Trial of Sodium Oxybate in Ethanol-Responsive Movement Disorders." Movement Disorders (2005); 20 (10): 1330-1337.
Gallimberti et al., "Clinical efficacy of gamma-hydroxybutyric acid in treatment of opiate withdrawal," EurArch Psychiatry Clin Neurosci. 1994;244(3):113-114.
Gallimberti et al., "Gamma-Hydroxybutyric Acid for Treatment of Opiate Withdrawal Syndrome," Neuropsychopharmacology, 1993, vol. 9, No. 1, pp. 77-81.
International Search Report and Written Opinion of the International Searching Authority for International Application No. PCT/US2019/062237, dated Mar. 31, 2020, 11 pages.
International Search Report and Written Opinion of the International Searching Authority for International Application No. PCT/US2020/066561, dated Apr. 13, 2021, 12 pages.
Jazz Pharmaceuticals, "Jazz Pharmaceuticals Announces Positive Top-line Results from Phase 3 Study of JZP-258 in Adult Narcolepsy Patients with Cataplexy and Excessive Daytime Sleepiness," Mar. 26, 2019, 2 pages, retrieved from https://investor.jazzpharma.com/node/16206/pdf.
Keating, GM, "Sodium Oxybate: A Review of Its Use in Alcohol Withdrawal Syndrome and in the Maintenance of Abstinence in Alcohol Dependence," Clinical Drug Investigation (2014) 34, 63-80.
Khediri et al., "Efficacy of Diosmectite (Smecta)® in the Treatment of Acute Watery Diarrhea in Adults: A Multicenter, Randomized, Double-Blind, Placebo-Controlled, Parallel Group Study," Hindawi Publishing Corporation, Gastroenterology Research and Practice, 2011, vol. 2011, Article ID 783196, 8 pages.
Lapierre et al., "The Effect of Gamma-Hydroxybutyrate: A Double-Blind Study of Normal Subjects," Sleep Research (1988); 17:99, 1988, 6 pages. (Abstract Only).
Lubrano, et al. "Fibromyalgia in Patients with Irritable Bowel Syndrome. An Association with the Severity of the Intestinal Disorder." Int J Colorectal Dis. (2001); 16 (4): 211-215.
Luhn, O., "Using Excipients in Powder Formulations," Pharmaceutical Technology Europe, Jan. 7, 2011, vol. 23, Issue 1, 6 pages, retrieved from https://www.pharmtech.com/view/using-excipients-powder-formulations.
Mahore et al. "Ion exchange resins: pharmaceutical applications and recent advancement." Int J Pharm Sci Rev Res (2010); 1.2: 8-13.
Mamelak, M., et al., "Treatment of Narcolepsy and Sleep Apnea with Gammahydroxybutyrate: A clinical and polysomnographic case study." Sleep (1981); 4 (1): 105-111.
Mamelak, M., et al., "Treatment of Narcolepsy with y-hydroxybutyrate. A review of Clinical and Sleep Laboratory Findings." Sleep (1986); 9 (1): 285-290.
Medicines for Children, "Oral Rehydration Salts," Leaflet information published Jul. 25, 2013, by Neonatal and Paediatric Pharmacists Group (NPPG), 6 pages, retrieved from https://www.medicinesforchildren.org.uk/oral-rehyd ration-salts.
Moldofsky et al. "A Chronobiologic Theory of Fibromyalgia." J. Muscoloskel. Pain, 1, 49 (1993).
Moldofsky, et al. "Musculoskeletal Symptoms and Non-REM Sleep Disturbance in Patients with 'Fibrositis Syndrome' and Healthy Subjects." Psychosom. Med. (1975); 37 (4): 341-351.

(56) References Cited

OTHER PUBLICATIONS

Morrison, Robert Thornton, et al., Organic Chemistry, 3rd Edition, (1973), pp. 672-677.
Ohta et al. "Development of a simple method for the preparation of a silica gel based controlled delivery system with a high drug content." European Journal of Pharmaceutical Sciences (2005); 26.1: 87-96.
Outlaw, et al. "Dyspepsia and its Overlap with Irritable Bowel Syndrome." Curr Gastroenterol Rep. (2006); 8 (4): 266-272.
Parmar et al., "Clinical Characteristics of Cataplectic Attacks in Type 1 Narcolepsy," Current Neurology and Neuroscience Reports (2020) 20:38, 9 pages.
Patil et al. "A review on ionotropic gelation method: novel approach for controlled gastroretentive gelispheres." International Journal of Pharmacy and Pharmaceutical Sciences (2012); 4.4: 27-32.
Puguan et al. "Diffusion characteristics of different molecular weight solutes in Ca-alginate gel beads." Colloids and Surfaces A: Physicochemical and Engineering Aspects (2015); 469:158-165.
Remington. The Science and Practice of Pharmacy. 20th Edition, Gennaro, Ed,. Lippincott Williams & Wilkins (2000). (See e.g. p. 861).
Remington. The Science and Practice of Pharmacy. 20th Edition, Gennaro, Ed,. Lippincott Williams & Wilkins. Chapter 45 (Oral Solid Dosage Forms) (2000) pp. 889-928.
Rohm and Haas. "Duolite AP143/1083 Pharmaceutical Grade Anion Exchange Resin." Feb. 2006, 4 pages.
Roxane Laboratories, Inc.'s Answer and Affirmative Defenses to Plaintiff's Complaint, (Jan. 4, 2013), 8 pages.
Roxane Laboratories, Inc.'s Answer, Affirmative Defenses and Counterclaims to Plaintiff's Complaint, (Dec. 29, 2010), 21 pages.
Roxane Laboratories, Inc.'s Answer, Affirmative Defenses and Counterclaims to Plaintiff's Complaint, (Jun. 1, 2011), 12 pages.
Roxane Laboratories, Inc.'s Answer, Affirmative Defenses and Counterclaims to Plaintiff's Complaint, (Mar. 9, 2011), 13 pages.
Roxane Laboratories, Inc.'s Answer, Affirmative Defenses and Counterclaims to Plaintiff's Complaint, (Nov. 9, 2012), 18 pages.
Roxane Laboratories, Inc.'s Initial Invalidity and Noninfringement Contentions Pursuant to Local Patent Rule 3.6, (Apr. 14, 2011), 317 pages.
Rubbens et al., "Gastric and Duodenal Ethanol Concentrations after intake of Alcoholic Beverages in Postprandial Conditions," Molecular Pharmaceutics, (2017) 14(12):4202-4208.
Scharf, M. B., et al., "GHB—New Hope for Narcoleptics?" Biol Psychiatry (1989); 26 (4): 329-330.
Scrima, L., et al., "Narcolepsy." New England J. Med. (1991); 324 (4): 270-272.
Seno and Yamabe. "The Rheological Behavior of Suspensions of Ion-exchange Resin Particles." Bulletin of the Chemical Society of Japan (1966); 39.4: 776-778.
Shah et al., "In vitro Dissolution Profile Comparison—Statistics and Analysis of the Similarity Factor, f2," Pharm Research, (1998) 15(6):889-896.
Singh et al. "Ion exchange resins: drug delivery and therapeutic applications." Fabad J. Pharm. Sci (2007); 32: 91-100.
Srikanth et al., "Ion-exchange resins as controlled drug delivery carriers." Journal of Scientific Research (2010); 2.3: 597-611.
Takka and Gürel. "Evaluation of chitosan/alginate beads using experimental design: formulation and in vitro characterization." AAPS PharmSciTech (2010); 11.1: 460-466.
The Dow Chemical Company, Product Data Sheet for AMBERLITE™ IRN78 Resin. Form No. 177-02230-0311, Rev. 0, 3 pages.
Thorpy, M.J., "Recently Approved and Upcoming Treatments for Narcolepsy," CNS Drugs (2020) 34:9-27.
Transcript of a Markman Hearing, dated Apr. 26, 2012, in the case of *Jazz Pharmaceuticals, Inc.*, Plaintiff, v. *Roxane Laboratories, Inc.*, Defendant (United States District Court for the District of New Jersey, Civil 106108 ES), (Apr. 26, 2012).
Turnberg, L.A. "Abnormalities in intestinal electrolyte transport in congenital chloridorrhoea." Gut. (1971); 12(7): 544-551.
U.S. Department of Health and Human Services et al., "Dissolution Testing of Immediate Release Solid Oral Dosage Forms," Food and Drug Administration, CDER, Aug. 1997, 17 pages.
U.S. Department of Health and Human Services et al., "Extended Release Oral Dosage Forms: Development, Evaluation, and Application of In Vitro/In Vivo Correlations", Food and Drug Administration, CDER, Sep. 1997, 27 pages.
Unknown author, title: definition of biotransformation; Medical dictionary; downloaded Jun. 21, 18 (Year: 2018), 3 pages.
Walden et al., "The Effect of Ethanol on the Release of Opioids 30 from Oral Sustained-Release Preparations," Drug Development and Industrial Pharmacy, 2007, 33:10,1101-1111.
Wermuth (Ed.), The Practice of Medicinal Chemistry, Academic Press, Third Edition, "Preparation of Water-Soluble Compounds Through Salt Formulation," Chapter 37, 2008, p. 758, 6 pages.
World Health Organization, "Annex 7: Multisource (generic) pharmaceutical products: guidelines on registration requirements to establish interchangeability," WHO Expert Committee on Specifications for Pharmaceutical Preparations Fortieth Report, pp. 347-390, 2006, retrieved from http://apps.who.int/prequal/info_general/documents/TRS937/WHO_TRS_937_eng.pdf#page=359.
Zheng (Ed.), "Formulation and Analytical Development for Low-Dose Oral Drug Products," John Wiley & Sons, Inc., Hoboken, New Jersey, Table 4.1, p. 65, 2009, 3 pages.
Arena, C., et al., "Absorption of Sodium Gamma-Hydroxybutyrate and its Prodrug Gamma-Butyrolactone: Relationship Between In Vitro Transport and In Vivo Absorption," Journal of Pharmaceutical Sciences, 1980, 69(3): 356-358.
Bédard, M.A., et al., "Nocturnal Gamma-Hydroxybutyrate—Effect on Periodic Leg Movements and Sleep Organization of Narcoleptic Patients", Clin Neuropharmacol., 1989, 12(1): 29-36.
Berner, Jon E., "A Case of Sodium Oxybate Treatment of Tardive Dyskinsela and Bipolar Diorder," J. Clin Psychiatry, 2008, 69: 862.
Berthier, M, et al., "Possible Involvement of a Gamma-Hydroxybutyric Acid Receptor in Startle Disease", Acta Paediatr, 1994, 83(6): 678-680.
Broughton, Roger, et al., "The Treatment of Narcolepsy-Cataplexy with Nocturnal Gamma-Hydroxybutyrate", Le Journal Canadien des Sciences Neurologiques, 1979, 6(1): 285-289.
Erowid, "Gamma-hydroxybutyrate (GHB) Basic Synthesis Procedure," http://www.crowid.ondchemicals/ghb/ghb svnthcsis.shtm (as downloaded on Aug. 8, 2013).
European Patent Office, European Search Report for European Application Serial No. 03075658.9, dated Apr. 11, 2003, 5 pg.
Ferrara, S.D., et al., "Pharmacokinetics of Gamma-Hydroxybutyric Acid in Alcohol Dependent Patients After Single and Repeated Oral Doses", Br. J. Clin. Pharmaca., 1992, 34(3): 231-235.
Ferris, Trevor J., et al., "Synthesis, characterisation and detection of gamma-hydroxybutyrate salts", Forensic Science International, 2012, 216: 158-162.
Fides, "Solutions of 4-hydroxybutyric acid salts for injection," Chem Abstract ES302338, Laboratorio M. Cuatecases, S.A., 2011, 2 pp.
Frucht, S.J., et al., "A Single-Blind, Open-Label Trial of Sodium Oxybate for Myoclonus and Essential Tremor," Neurology, 2005, 65: 1967-1970.
Gallimberti, L., et al., "Gamma-Hydroxybutric Acid in the Treatment of Alcohol Dependence: A Double-Blind Study", Alcohol Clin. Exp. Res., 1992, 16(4): 673-676.
Gallimberti, L., et al., "Gamma-hydroxybutyric Acid for Treatment of Alcohol Withdrawal Syndrome", Clinical Pharmacology, 1989, 2(8666): 787-789.
Geekwench et al., "Title: Does anyone know why Jazz choose to make sodium oxybate?", Sep. 14, 2010; downloaded from http://www.talkaboutsleep.com/message/boards/topic/does-anybody-know-why-jazz-chose-to-make-sodium-oxybate/#sthash.no0PSCkL.dpuf on Jan. 21, 2015.
Geekwench et al., "Title: Does anyone know why Jazz choose to make sodium oxybate?", Sep. 14, 2010; downloaded from http://www.talkaboutsleep.com/message-boards/topic/does-anybody-know-why-jazz-chose-to-make-sodium-oxybate/ on Nov. 13, 2017 (30 pages).

(56) References Cited

OTHER PUBLICATIONS

Gerra, G., et al., "Flumazenil effects on growth hormone response to gammahydroxybutyric acid", Int Clin Psychopharmacol., 1994, 9(3): 211-215.

Gessa, G.L., "Gamma-Hydroxybutyric Acid in the Treatment of Alcohol Dependence", Clin. Neuropharm., 15 Suppl. 1, Pt. A, (1992), 303a-304a.

Gessa, Gian Luigi, et al., "Gamma-hydroxybutyric acid (GHB) for treatment of ethanol dependence", European Neuropsychopharmacology, 1993, 3(3): 224-225.

Grove-White, I.G., et al., "Critical Flicker Frequency after Small Doses of Methohexitone, Diazepam and Sodium 4-Hydroxybutyrate", Brit. J. Anaesth, 1971, 43(2): 110-112.

Grove-White, I.G., et al., "Effect of Methohexitone, Diazepam and Sodium 4-Hydroxybutyrate on Short-Term Memory", Brit. J. Anaesth., 1971, 43: 113-116.

Hasenbos, M A, "Anaesthesia for bullectomy. A technique with spontaneous ventilation and extradural blockade", Anaesthesia, 1985, 40(10): 977-980.

Hoes, M.J.A.J.M., et al., "Gamma-hydroxybutyric acid as hypnotic. Clinical and pharmacokinetic evaluation of gamma-hydroxybutyric acid as hypnotic in man", Encephale, 1980, 6(1): 93-99.

International Searching Authority, "International Search Report, dated Apr. 15, 2014, for Internaitonal Patent Application No. PCT/US2013/074954".

International Searching Authority, "Written Opinion, dated Apr. 15, 2014, for International Patent Application No. PCT/US2013/074954".

International Searching Authority, International Search Report and Written Opinion, dated Jun. 27, 2018, for International Patent Application No. PCT/EP2018/056745 (12 pages).

International Searching Authority, International Search Report for International Application Serial No. PCT/US99/30740, dated Jul. 21, 2000, 1 pg.

Jazz Pharmaceuticals, Inc., "XYREM® (sodium oxybate) oral solution Prescribing Information," XYREM® US Package Insert available at http://pp.jazzpharma.com/pi/xyrem.en.USPI.pdf (downloaded Sep. 12, 2017).

Jurkovich, Patti, Amendment filed in response to Written Opinion, International Application Serial No. PCT/US99/30740, filed Feb. 16, 2001, 9 pg.

Laborit, H., "Gamma-Hydroxybutyrate, Succinic Semialdehyde and Sleep," Laboratoire d'Eutonologie, 1973, 8: 257-274.

Ladinsky, Herbert, et al., "Mode of Action of Gamma-Butyrolactone on the Central Cholinergic System," Naunyn-Schmiedeberg's Arch. Pharmacal., 1983, 322: 42-48.

Lammers, G.J., et al., "Gammahydroxybutyrate and Narcolepsy: A Double-Blind Placebo-Controlled Study," Sleep, 1993, 16(3): 216-220.

Lapierre, O., et al., "The Effect of Gamma-Hydroxybutyrate on Nocturnal and Diurnal Sleep of Normal Subjects: Further Considerations on REM Sleep-Triggering Mechanisms," Sleep, 1990, 13(1): 24-30.

Lee, C.R., "Evidence for the Beta-Oxidation of Orally Administered 4-Hydroxybutyrate in Humans", Biochemical Medicine, 1977, 17(3): 284-291.

Lettieri, John, et al., "Improved Pharmacological Activity via Pro-Drug Modification: Comparative Pharmacokinetics of Sodium Gamm-Hydroxybutyrate and Gamma-Butyrolactone", Research Communications in Chemical Pathology and Pharmacology, 1978, 22(1): 107-118,.

Lynch, M., "Malic Acid", The Handbook of Pharmaceutical Excipients, 2nd Ed., 1994, 63 3: 285-286.

Mamelak, M., et al., "Sleep-Inducing Effects of Gam-mahydroxybutyrate", The Lancet, 1973, 2(7824): 328-329.

Mamelak, Mortimer, "Gammahydroxybutyrate: An Endogenous Regulator of Energy Metabolism", Neuroscience and Biobehavioral Reviews, 1989, 13(4): 187-198.

Mamelak, Morty, et al., "The Effects of Gamma-Hydroxybutyrate on Sleep", Biological Psychiatry, 1977, 12(2): 273-288.

Morrison, Robert T., et al., "Organic Chemistry", Chapter 20: "Functional Derivatives of Carboxylic Acids," 3rd Edition, 1973, pp. 658-700.

Nema, Sandeep, et al., "Excipients and Their Use in Injectable Products", PDA J. Pharm. Sci. Technol, 1997, 51(4): 166-171.

Neuman, Ariel, "GHB's Path to Legitimacy: An Administrative and Legislative History of Xyrem", paper submitted to Harvard Law School, 2004, 1-39.

Ondo, William G., et al., "Sodium Oxybate for Excessive Daytime Sleepiness in Parkinson Disease," Arch. Neural., 2008, 65(10): 1337-1340.

Palatini, P., et al., "Dose-Dependent Absorption and Elimination of Gamma-Hydroxybutyric Acid in Healthy Volunteers", Eur. J. Clin Pharmacal., 1993, 45(4): 353-356.

Roth, R. H., et al., "Gamma-Butyrolactone and Gamma-Hydroxybutyric Acid-II. The Pharmacologically Active Form", J. Neuropharmacol. 1966, 5: 421-428.

Roth, Robert H., et al., "Gamma-Butyrolactone and Gamma-Hydroxybutyric Acid-I, Distribution and Metabolism", Biochemical Pharmacology, 1966, 15: 1333-1348.

Russel, I. Jon, et al., "Sodium Oxybate Relieves Pain and Improves Function in Fibromyaligia Syndrome," Arthritis. Rheum , 2009, 60: 299-309.

Scharf et al., "Effect of Gamma-Hydroxybutyrate on Pain, Fatigue, and the Alpha Sleep Anomaly in Patients with Fibromyalgia. Preliminary Report", The Journal of Rheumatology, 25(10): 1986-1990 (1998).

Scharf, M.B., et al., "The Effects and Effectiveness of Gamma-Hydroxybutyrate in Patients with Narcolepsy", J. Clin. Psychiatry, 1985, 46(6): 222-225.

Scharf, Martin B., et al., The Effects of Sodium Oxybate on Clinical Symptoms and Sleep Patterns in Patients with Fibromyalgia, J. Rheumatol, 2003, 30(5): 1070-1074.

Scrima, et al., "Effect of High Altitude on a Patient with Obstructive Sleep Apnea", Sleep Research, Abstract, 1987, 16: 427.

Scrima, et al., "Effects of Gamma-Hydroxybutyrate (GHB) on Narcolepsy-Cataplexy Symptoms and MSLT Results in Male and Female Patients", Association of Professional Sleep Societies, Abstract, 1988, 251.

Scrima, et al., "Gamma-Hydroxybutyrate Effects on Cataplexy and Sleep Attacks in Narcoleptics", Sleep Research, Abstract, 1987, 16: 134.

Scrima, L, et al., "Efficacy of Gamma-Hydroxybutyrate Versus Placebo in Treating Narcolepsy-Cataplexy: Double-Blind Subjective Measures", Biol. Psychiatry, 1989, 26(4): 331-343.

Scrima, L. et al., "Effect of Gamma-Hydroxybutyrate on a Patient with Obstructive Sleep Apnea," Sleep Research, Abstract, 1987, 16: 137.

Scrima, Lawrence, et al., "The Effects of Gamma-Hydroxybutyrate on the Sleep of Narcolepsy Patients: A Double-Blind Study", Sleep, 1990, 13(6): 479-490.

Sériès, F., et al., "Effects of Enhancing Slow-Wave Sleep by Gamma-Hydroxybutyrate on Obstructive Sleep Apnea", Am. Rev. Respir. Dis., 1992, 145(6): 1378-1383.

Snead, O. Carter et al., "Ontogeny of Gamma-Hydroxybutyric Acid. I. Regional Concentration in Developing Rat, Money and Human Brain," Brain Res., 1981, 227(4): 579-589.

Snead, O. Carter, "Gamma-Hydroxybutyrate Model of Generalized Absence Seizures: Further Characterization and Comparison with Other Absence Models," Epilepsia, 1988, 29(4): 361-368.

Stock, Günter, et al., "Increase in Brain Dopamine after Axotomy or Treatment with Gammahydroxybutyric Acid Due to Elimination of the Nerve Impulse Flow", Naunyn-Schmiedeberg's Arch, Pharmacal., 1973, 278(4): 347-361,.

Strong, A. J., "Gamma-Hydroxybutyric Acid and Intracranial Pressure", The Lancet, 1984, 1(8389): 1304.

Suner, S., et al., "Pediatric Gamma Hydroxybutyrate Intoxication", Acad. Emerg. Med., 1997, 4(11): 1041-1045.

Tunnicliff, Godfrey, "Sites of Action of Gamma-Hydroxybutyrate (GHB)—A Neuroactive Drug with Abuse Potential", Clinical Toxicology, 1997, 35(6): 581-590.

(56) References Cited

OTHER PUBLICATIONS

United States District Court, "Opinion," *Jazz Pharmaceuticals, Inc. v. Roxane Laboratories, Inc.*, Markman Hearing, No. 10-6108 (ES), (Sep. 14, 2012), 43 pg.

United States District Court, "Order," *Jazz Pharmaceuticals, Inc. v. Roxane Laboratories, Inc.*, Markman Hearing, No. 10-6108 (ES), (Sep. 14, 2012), 1 pg.

United States Pharmacopeia (USP), Pharmaceutic Ingredients, 23/NF18, 1995, p. 2205.

Van Den Bogert, et al., "Placentatransfer of 4-Hydroxybutyric Acid in Man", Anaesthesiology and Intensive Care Medicine, 1978, 110: 55-64.

Vickers, M.D., "Gammahydroxybutyric Acid", Int. Anesth. Clinic, 1969, 7(1): 75-89.

Vogel et al., 2018, "Toxicologic/transport properties of NCS-382, a γ-hydroxybutyrate (GHB) receptor ligand, in neuronal and epithelial cells: Therapeutic implications for SSADH deficiency, a GABA metabolic disorder," Toxicol In Vitro, 46:203-212 (Epub 2017),.

Yamada, Y., et al., "Effect of Butyrolactone and Gamma-Hydroxybutyrate on the EEG and Sleep Cycle in Man", Electroenceph. clin. Neurophysiol., 1967, 22: 558-562.

Chen et al., "Pharmacokinetics, relative bioavailability and food effect of JZP-258 and sodium oxybate: results of two phase 1, open-label, randomised crossover studies in healthy volunteers," Sleep Medicine, Abstracts, 2019, vol. 64, pp. S65-S66.

International Search Report and Written Opinion of the International Searching Authority for International Application No. PCT/US2021/019024, dated Jun. 2, 2021, 10 pages.

Jha, M.K, "Modified release formulations to achieve the quality target product profile (QTPP)," IJPSR, 2012; vol. 3(8): 2376-2386.

Rujivipat et al., "Improved drug delivery to the lower intestinal tract with tablets compression-coated with enteric/nonenteric polymer powder blends," European Journal of Pharmaceutics and Biopharmaceutics (2010) 76: 486-492.

Non-Final Office Action dated Aug. 25, 2021, for U.S. Appl. No. 17/222,579, 14 pages.

\* cited by examiner

GAMMA-HYDROXYBUTYRATE COMPOSITIONS AND THEIR USE FOR THE TREATMENT OF DISORDERS

1. CROSS REFERENCE

This application is a continuation of U.S. patent application Ser. No. 16/575,213, filed Sep. 18, 2019, which is a continuation of U.S. patent application Ser. No. 15/709,262, filed Sep. 19, 2017, now abandoned, which claims the benefit of U.S. Provisional Patent Application No. 62/473,232, filed Mar. 17, 2017, the content of each of which is incorporated herein by reference in its entirety.

2. FIELD OF THE INVENTION

Provided herein are pharmaceutical compositions and formulations comprising salts of gamma-hydroxybutyrate (GHB). In one embodiment, the salts encompass more than one type of cation. Also provided herein are methods of making the pharmaceutical compositions and formulations, and methods of the treatment of disorders including fibromyalgia and sleep disorders. Also described herein is that such pharmaceutical compositions and formulations are for treating diseases or disorders including fibromyalgia and sleep disorders. Such sleep disorders include apnea, sleep time disturbances, narcolepsy, cataplexy, sleep paralysis, hypnagogic hallucination, sleep arousal, insomnia, and nocturnal myoclonus.

3. BACKGROUND OF THE INVENTION

Sodium oxybate (Na.GHB), commercially sold as Xyrem® (Jazz Pharmaceuticals), is approved for the treatment of excessive daytime sleepiness and cataplexy in patients with narcolepsy. Na.GHB has also been reported to be effective for relieving pain and improving function in patients with fibromyalgia syndrome (See Scharf et al., 2003, *J. Rheumatol.* 30: 1070; Russell et al., 2009, *Arthritis. Rheum.* 60: 299), and in alleviating excessive daytime sleepiness and fatigue in patients with Parkinson's disease, improving myoclonus and essential tremor, and reducing tardive dyskinesia and bipolar disorder (See Ondo et al., 2008, *Arch. Neural.* 65: 1337; Frucht et al., 2005, *Neurology* 65: 1967; Berner, 2008, *J. Clin. Psychiatry* 69: 862).

Xyrem®, for use with patients with narcolepsy, is a chronically used product which requires high levels of the drug. The amount of sodium intake from the drug significantly increases the daily sodium intake for patients, which is undesirable for patients with hypertension, heart disease, renal disease or at risk of stroke.

Since Xyrem® is administered to a broad population, there is a need for GHB formulations that minimize the undesirable side effects of the sodium, particularly in patients with hypertension, heart disease, renal disease or at risk of stroke, yet provide additional health benefits from the presence of the other salts. It is desirable that such modified formulations provide good solubility, stability and purity in order to provide safe, effective and consistent doses to patients, and also display acceptable pharmacodynamic and pharmacokinetic properties. See U.S. Pat. Nos. 8,591,922; 8,901,173; and 9,132,107; which are incorporated by reference in their entireties.

4. SUMMARY OF THE INVENTION

Provided herein are pharmaceutical compositions and formulations comprising salts of gamma-hydroxybutyrate ("GHB") which are useful in the treatment of conditions responsive to GHB, for example, fibromyalgia and sleep disorders such as apnea, sleep time disturbances, narcolepsy, excessive daytime sleepiness (EDS) cataplexy, sleep paralysis, hypnagogic hallucination, sleep arousal, insomnia, and nocturnal myoclonus.

One embodiment, as provided herein, is a GHB formulation with a reduction in sodium content. Another embodiment, as provided herein, is a GHB formulation with a reduced sodium content and which is bioequivalent to Xyrem®. In certain embodiments, the reduction in sodium content involves use of other cations such as potassium, calcium, magnesium, and others.

For convenience in comparing various salt compositions at the same oxybate or GHB molar dose, compositions expressed as percentages in this application refer to molar equivalent percentage (% molar equivalents) of each salt of oxybate or GHB. This is usually close to, but not the same as, a composition that would be expressed as wt/wt %. As used herein, the terms "oxybate" and "GHB" are used interchangeably.

Accordingly, in one aspect, provided herein are pharmaceutical compositions and formulations comprising salts of GHB. In one embodiment, the formulation is a pharmaceutical composition of GHB comprising a mixture of two or more salts of GHB, wherein the mixture comprises at least 50% of a sodium salt of gamma-hydroxybutyrate (Na.GHB), and wherein the mixture further comprises one or more of a potassium salt of gamma-hydroxybutyrate (K.GHB) and a calcium salt of gamma-hydroxybutyrate (Ca.(GHB)$_2$). In certain embodiments, the Na.GHB salt is present in the mixture in about 50%, and up to 55%, 60%, 70% or 80%. In certain embodiments, the pharmaceutical composition does not comprise a substantial amount of a magnesium salt of gamma-hydroxybutyrate (Mg.(GHB)$_2$).

In another embodiment the pharmaceutical composition is given to the patient in an aqueous solution with a volume of between 25 and 100 mL, 25 and 75 mL, or 55 and 65 mL.

In another embodiment, the pharmaceutical composition, when administered to a patient, is bioequivalent to the average maximum GHB plasma concentration (Cmax) and the average maximum GHB plasma area under the curve (AUC) of the Cmax of Na.GHB within 80% to 125%.

In another embodiment, the pharmaceutical composition comprises a mixture of three salts of GHB, wherein the mixture comprises at least 50% of Na.GHB, and further comprises K.GHB and Ca.(GHB)$_2$. In certain embodiments, the pharmaceutical composition comprises a mixture of three GHB salts, wherein the mixture comprises between 50 and 60% of Na.GHB, and further comprises between 20 and 40% K.GHB, and between 10 and 20% Ca.(GHB)$_2$. In certain embodiments, the pharmaceutical composition comprises a mixture of three GHB salts, wherein the mixture comprises about 50% of Na.GHB, 34% K.GHB, and 16% Ca.(GHB)$_2$ for each GHB salt.

In another embodiment, the pharmaceutical compositions and/or formulations disclosed herein can be used to treat a disease or condition selected from the group consisting of a sleeping disorder, drug abuse, alcohol and opiate withdrawal, a reduced level of growth hormone, anxiety, analgesia, a neurological disorder (e.g., Parkinson's Disease and depression), an endocrine disturbance, hypoxia or anoxia of tissues (such as from stroke or myocardial infarction), or an increased level of intracranial pressure.

In another embodiment, the pharmaceutical compositions disclosed herein comprise less than 100 mL of an aqueous solution, wherein the aqueous solution comprises a mixture of two or more GHB salts, the mixture comprising between 40% to 50% Na.GHB and further comprising one or more salts selected from K.GHB, Ca.(GHB)$_2$, and Mg.(GHB)$_2$. In certain embodiments, the pharmaceutical compositions disclosed herein do not comprise a substantial amount Ca. (GHB)$_2$) or Mg.(GHB)$_2$.

In another embodiment, the pharmaceutical composition comprises about 8% Na.GHB, 23% K.GHB, 48% Ca. (GHB)$_2$ and 21% Mg.(GHB)$_2$. In certain embodiments, this pharmaceutical composition can be used to treat the diseases or conditions listed above.

In another embodiment, the pharmaceutical compositions and/or formulations disclosed herein, when administered to a patient, have a lower average maximum GHB plasma concentration (Cmax) than the Cmax of Na.GHB.

Xyrem®, as disclosed herein, is a commercially sold product comprised of 100% sodium oxybate (Na.GHB), and is prescribed for twice nightly use for the treatment of excessive daytime sleepiness and cataplexy in patients with narcolepsy. Accordingly, in another aspect, provided herein is a first dose of a first pharmaceutical composition and/or formulation having a Na.GHB of less than 50% and a second dose of a second pharmaceutical composition and/or formulation having a Na.GHB above 50%. Another embodiment has the doses in reverse order and a further embodiment uses similar doses of either formulation. In certain embodiments, the first dose can be administered within 4 hours of eating and produces a GHB Cmax lower than the Cmax of Na.GHB, but may have less of a food effect.

In another aspect, the pharmaceutical compositions and formulations provided herein can be used to treat a disease or condition selected from the group consisting of a sleeping disorder, drug abuse, alcohol and opiate withdrawal, a reduced level of growth hormone, anxiety, analgesia, a neurological disorder (e.g., Parkinson's Disease and depression), an endocrine disturbance, hypoxia or anoxia of tissues (such as from stroke or myocardial infarction), or an increased level of intracranial pressure. In one embodiment, the formulations and pharmaceutical compositions provided herein can be used to treat conditions responsive to GHB, for example, fibromyalgia and sleep disorders such as apnea, sleep time disturbances, narcolepsy, cataplexy, excessive daytime sleepiness (EDS), sleep paralysis, hypnagogic hallucination, sleep arousal, insomnia, and nocturnal myoclonus.

The pharmaceutical compositions and formulations disclosed herein is for use in a method of treating a disease or condition selected from the group consisting of a sleeping disorder, drug abuse, alcohol and opiate withdrawal, a reduced level of growth hormone, anxiety, analgesia, a neurological disorder (e.g. Parkinson's Disease and depression), an endocrine disturbance, hypoxia or anoxia of tissues (such as from stroke or myocardial infarction), or an increased level of intracranial pressure. In certain embodiment, the formulations and pharmaceutical compositions disclosed herein are used in a method of treating conditions responsive to GHB, for example, fibromyalgia and sleep disorders such as apnea, sleep time disturbances, narcolepsy, cataplexy, excessive daytime sleepiness (EDS), sleep paralysis, hypnagogic hallucination, sleep arousal, insomnia, and nocturnal myoclonus.

In another aspect, provided herein are methods of treating a disease or condition in a patient that is suitable for treatment with GHB, comprising administering to the patient the pharmaceutical compositions and formulations disclosed herein. In certain embodiments, the disease or condition is selected from the group consisting of a sleeping disorder, drug abuse, alcohol and opiate withdrawal, a reduced level of growth hormone, anxiety, analgesia, a neurological disorder (e.g., Parkinson's Disease and depression), an endocrine disturbance, hypoxia or anoxia of tissues (such as from stroke or myocardial infarction), or an increased level of intracranial pressure. In certain embodiments, the disease or condition is elected from the group consisting of fibromyalgia and sleep disorders such as apnea, sleep time disturbances, narcolepsy, cataplexy, excessive daytime sleepiness (EDS), sleep paralysis, hypnagogic hallucination, sleep arousal, insomnia, and nocturnal myoclonus.

In another embodiment, methods of treatment disclosed herein comprises one or more steps, as follows: (i) diluting an aqueous solution comprising a mixture of two or more GHB salts, the mixture comprising less than 50% Na.GHB, and further comprising one or more salts selected from K.GHB, Ca.(GHB)$_2$, and Mg.(GHB)$_2$, to provide a first dose of GHB salts; (ii) diluting an aqueous solution comprising a mixture of two or more GHB salts, the mixture comprising from about 50% to about 80% of Na.GHB, and further comprising one or more salts selected from K.GHB, Ca. (GHB)$_2$, and Mg.(GHB)$_2$, to provide a second dose of GHB salts; (iii) orally administering to a patient having a disease or condition that is suitable for treatment with GHB the first dose; and (iv) orally administering to the patient the second dose within 2.5 to 4 hours following the first dose.

The pharmaceutical compositions and formulations disclosed herein is for use in a method of treating a disease or condition in a patient that is suitable for treatment with GHB, comprising administering to the patient the pharmaceutical compositions and formulations disclosed herein.

In certain embodiments, the pharmaceutical compositions and formulations disclosed herein is for use in a method of treating a disease or condition in a patient further comprises one or more steps, as follows: (i) diluting an aqueous solution comprising a mixture of two or more GHB salts, the mixture comprising less than 50% Na.GHB, and further comprising one or more salts selected from K.GHB, Ca. (GHB)$_2$, and Mg.(GHB)$_2$, to provide a first dose of GHB salts; (ii) diluting an aqueous solution comprising a mixture of two or more GHB salts, the mixture comprising from about 50% to about 80% of Na.GHB, and further comprising one or more salts selected from K.GHB, Ca.(GHB)$_2$, and Mg.(GHB)$_2$, to provide a second dose of GHB salts; (iii) orally administering to a patient having a disease or condition that is suitable for treatment with GHB the first dose; and (iv) orally administering to the patient the second dose within 2.5 to 4 hours following the first dose.

In other aspects, provided herein are methods of making the pharmaceutical compositions disclosed herein.

5. BRIEF DESCRIPTION OF THE FIGURES

FIG. 1 shows the plasma GHB concentration vs time for Formulation "O" (8% Na.GHB, 23% K.GHB, 48% Ca. (GHB), and 21% Mg.(GHB)$_2$) compared to Xyrem® ("X") given in either the fed or fasted state (✦, Xyrem® fasted; ✦, Formulation "O" fasted; ✦ Xyrem® fed; ✦, Formulation "O" fed). The objective was to characterize bioequivalence of Formulation "O" to Xyrem®.

Figure 2:
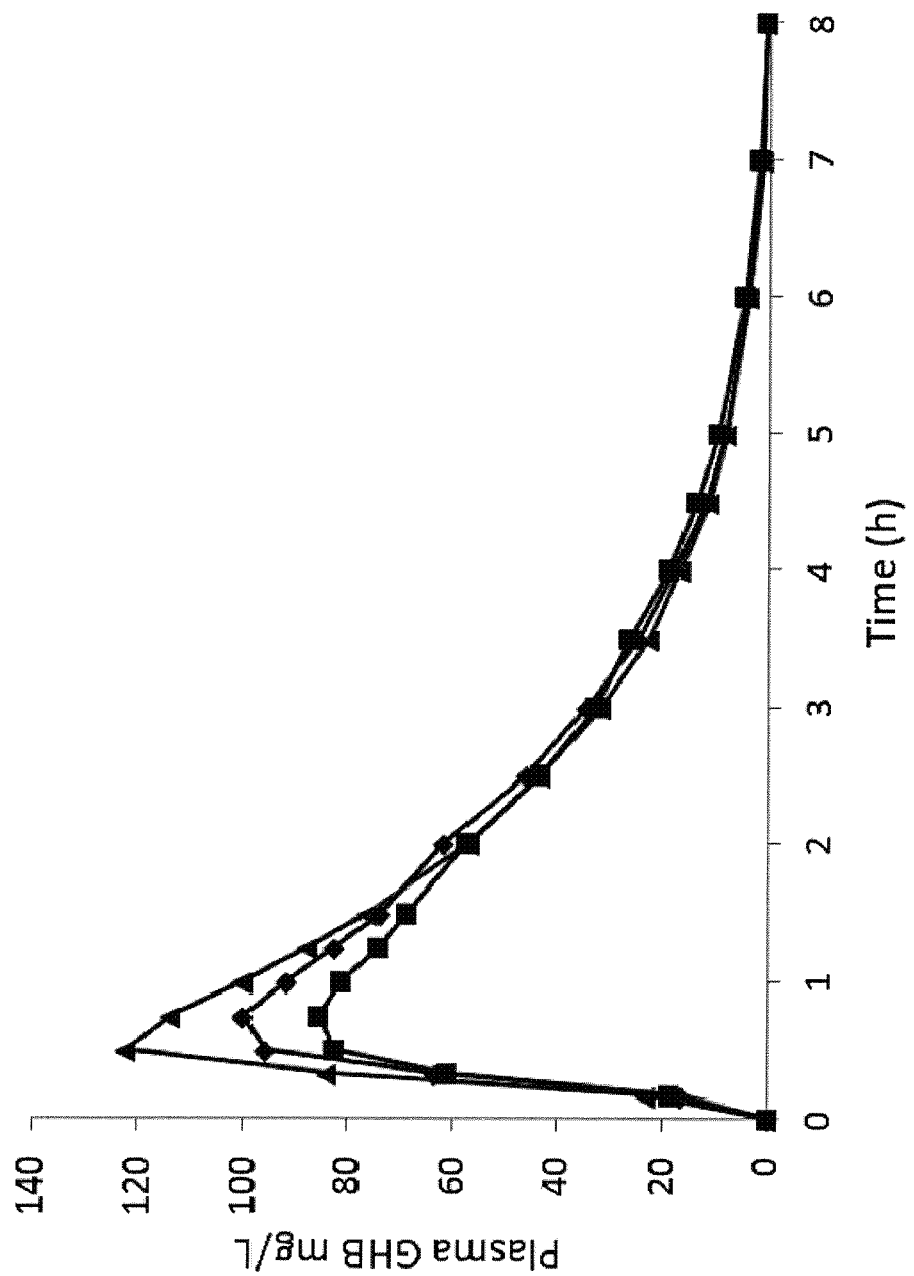

FIG. 2 shows the plasma GHB concentration vs time for blends of Formulation "O" and Xyrem® ("X") in proportions of 100% Xyrem®, 44% Xyrem®, and 17% Xyrem®, respectively (✦, fasted 4.5 g "X"; ✦, fasted 2.5 g "O"+2.0 g "X"; ✦, fasted 3.75 g "O"+0.75 g "X"). The objective was to determine how much sodium (or Xyrem®) would be required to achieve bioequivalence in the fasted state.

Figure 3:
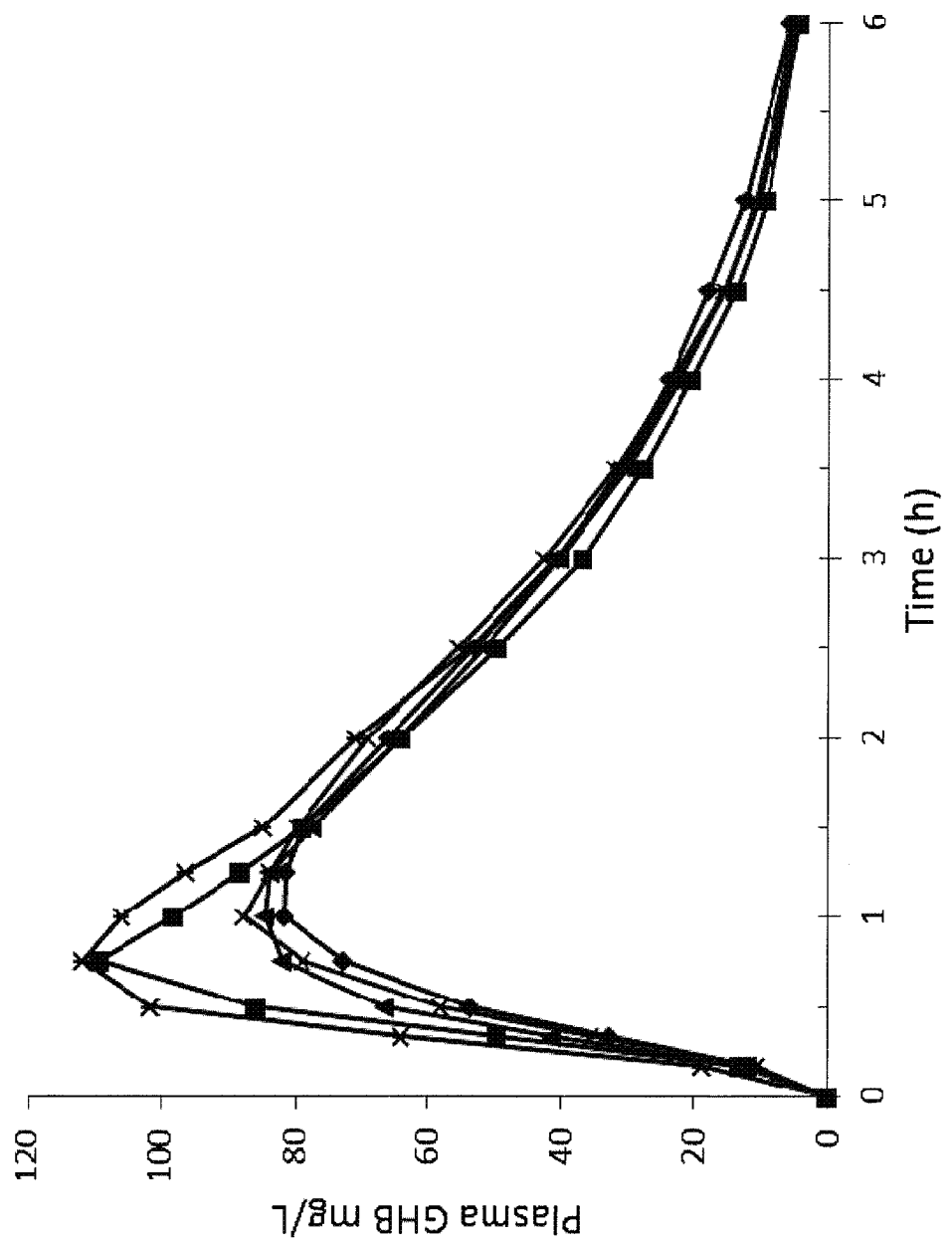

FIG. 3 shows the plasma GHB concentration vs time for various mixed oxybate salt formulations compared to Xyrem® in the fasted state where both are given at a lower volume of administration of 60 mL (—✦—, Xyrem® (100% Na); —■—, Formulation 507D (50% Na, 34% K, 16% Ca, 0% Mg); —✱—, 507C (33% Na, 0% K, 48% Ca, 19% Mg); —▲—, 507A (33% Na, 34% K, 33% Ca, 0% Mg); —◆—, 507G (23% Na, 19% K, 40% Ca, 18% Mg)).

Figure 4B:
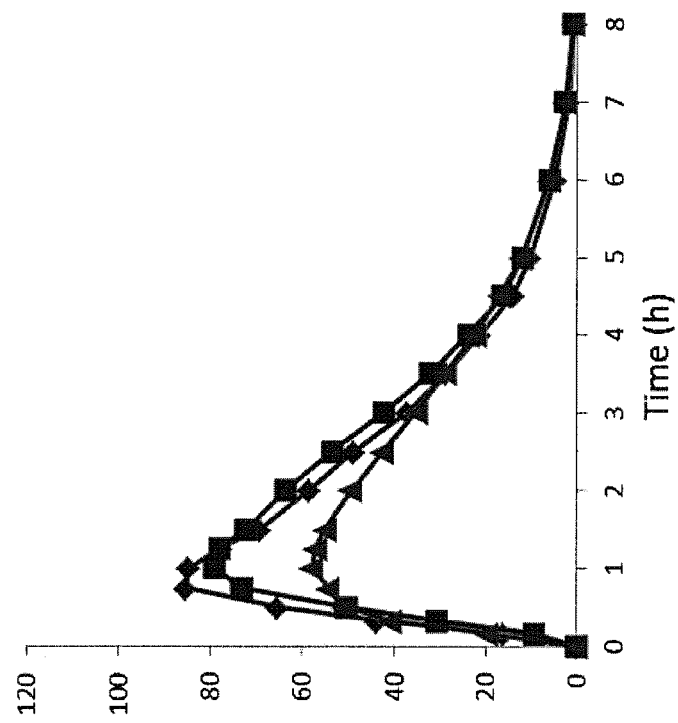
Figure 4A:
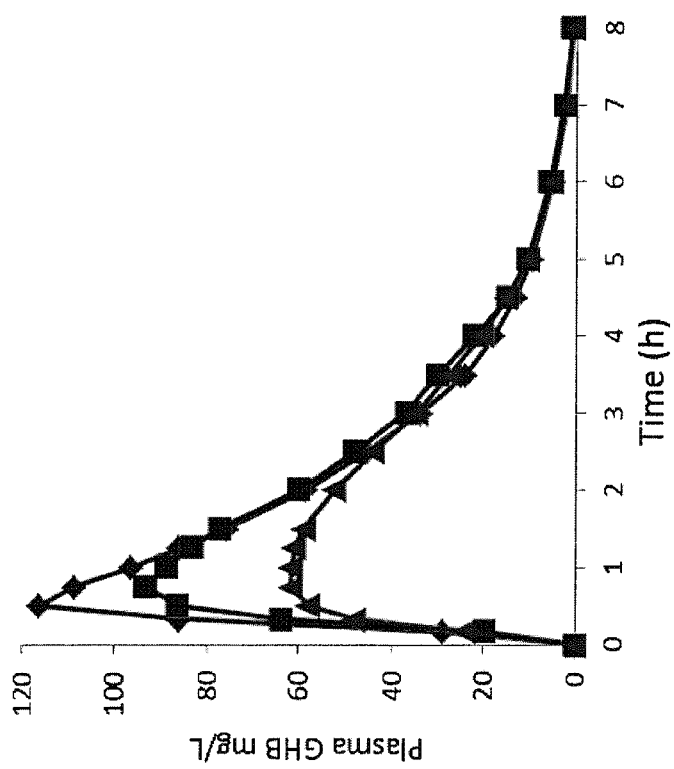

FIG. 4A-4B compare Xyrem® and Formulation "O" when given fasted with 60 mL or 240 mL water or when given fed with 60 mL water. FIG. 4A. (Left) Plasma GHB concentration when Xyrem® was given (fasted) with 60 mL or 240 mL water or when Xyrem® was given (fed) with 60 mL water (—◆—, fasted 240 mL; —■—, fasted 60 mL; —▲—, fed 60 mL). FIG. 4B (Right) Plasma GHB concentration when Formulation "O" was given (fasted) with 60 mL or 240 mL water or when Formulation "O" was given (fed) with 60 mL water (—◆—, fasted 240 mL; —■—, fasted 60 mL; —▲—, fed 60 mL).

Figure 5A:
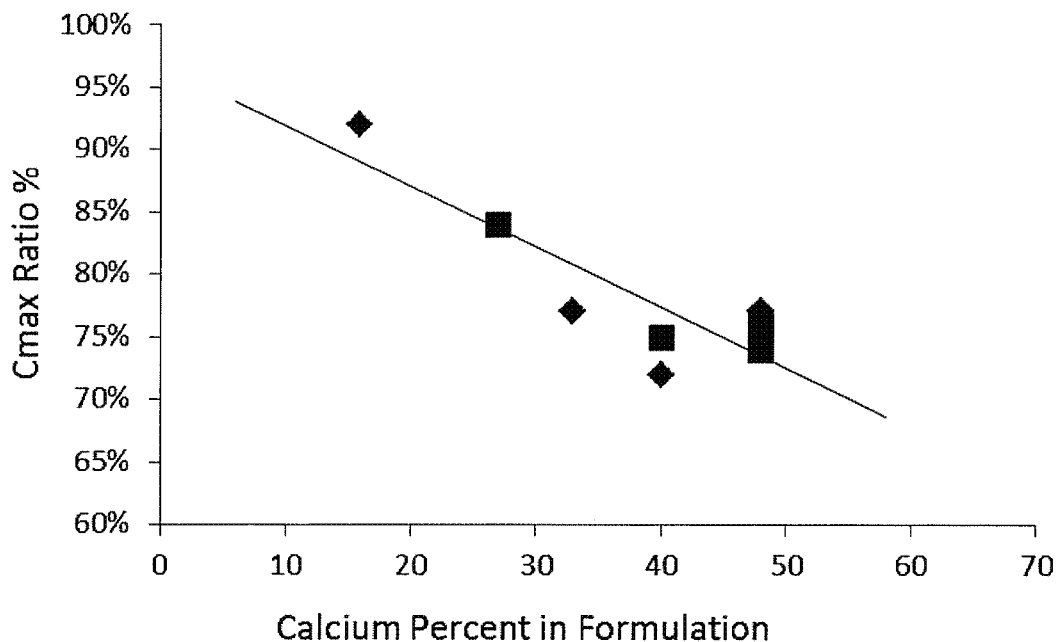
Figure 5B:
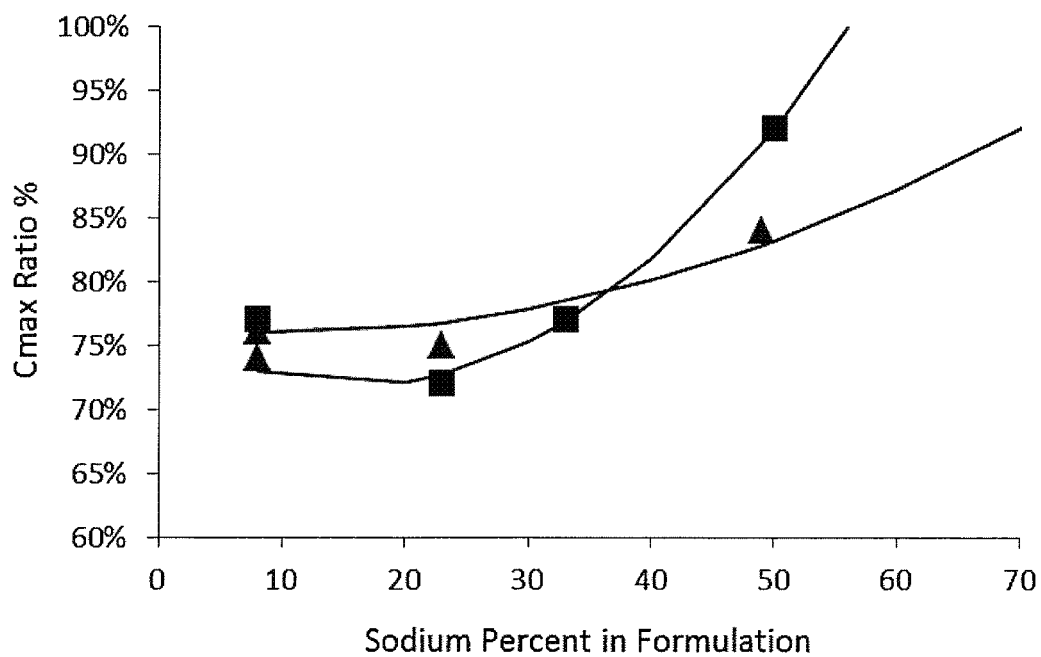

FIG. 5A-5B show the relationship between Cmax ratio (to Xyrem®) and calcium content or sodium content of the example formulations subjected to fasted-state PK evaluations when administered in either 240 mL aqueous volume or 60 mL aqueous volume. FIG. 5A. (Top) Relationship between Cmax ratio (to Xyrem®) and calcium content of the example formulations subjected to fasted-state PK evaluations when administered in either 240 mL aqueous volume (—◆—, Cmax, 60 mL; —■—, Cmax, 240 mL). FIG. 5B (Bottom) Relationship between Cmax ratio (to Xyrem®) and sodium content of the example formulations subjected to fasted-state PK evaluations when administered in either 240 mL aqueous volume (—■—, Cmax, 60 mL; —▲—, Cmax, 240 mL).

Figure 6:
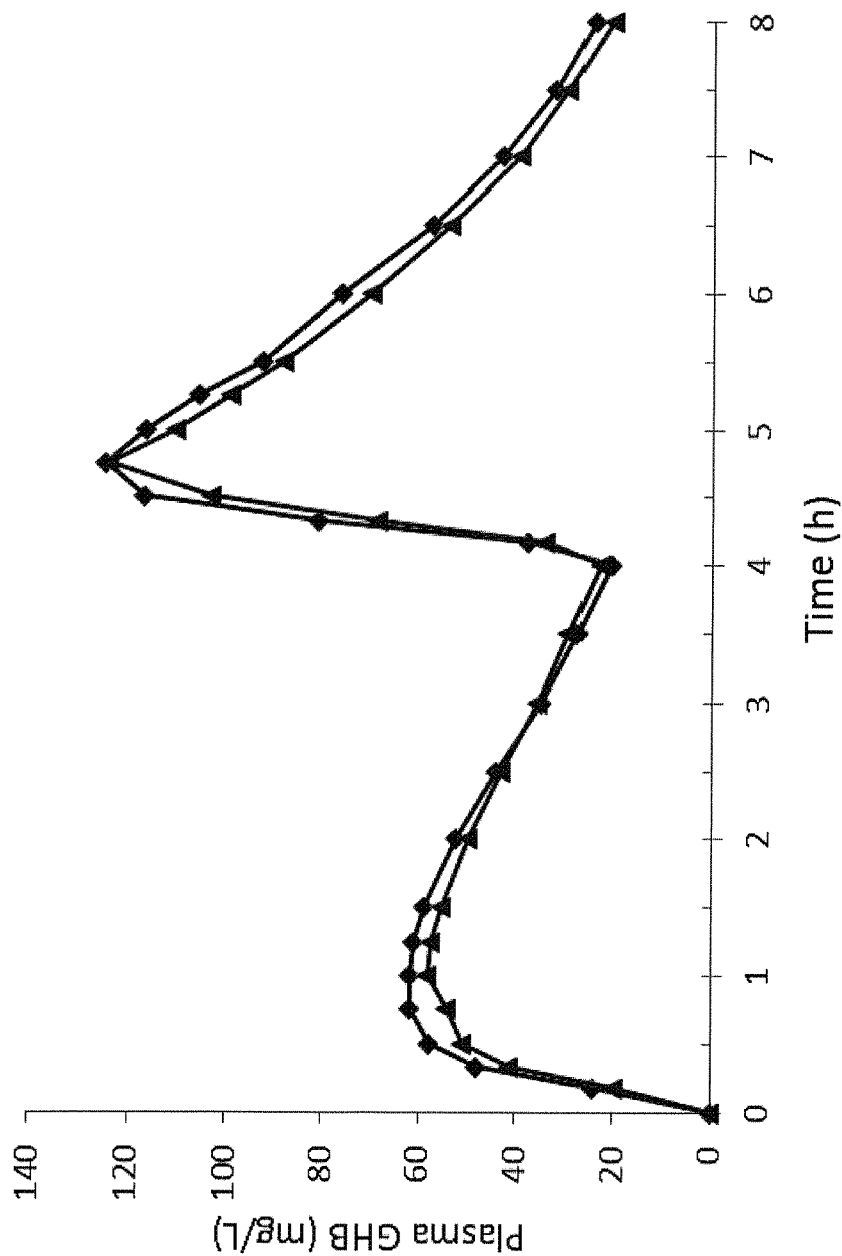

FIG. 6 is a graph showing the expected behavior of taking separate formulations as part of an equally divided dose given 4 h apart (—◆—, 1st dose Xyrem® fed, 2nd dose Xyrem® fasted; —▲—, 1st dose Formulation "O" fed, 2nd dose Formulation 507D fasted). Formulation "O" is given initially and then formulation "507D" is given 4 h later. This is compared to Xyrem® given both times.

6. DETAILED DESCRIPTION OF THE INVENTION

Gamma-hydroxybutyrate (GHB), also known as "oxybate," is an endogenous compound with hypnotic properties that is found in human body tissues, such as the mammalian brain. In the brain, the highest GHB concentration is found in the hypothalamus and basal ganglia and GHB is postulated to function as a neurotransmitter (See Snead and Morley, 1981, *Brain Res.* 227(4): 579-89). The neuropharmacologic effects of GHB include increases in brain acetylcholine, increases in brain dopamine, inhibition of GABA-ketoglutarate transaminase and depression of glucose utilization but not oxygen consumption in the brain. GHB treatment substantially reduces the signs and symptoms of narcolepsy, i.e., daytime sleepiness, cataplexy, sleep paralysis, and hypnagogic hallucinations. In addition, GHB increases total sleep time and REM sleep, and it decreases REM latency, reduces sleep apnea, and improves general anesthesia (see, e.g., U.S. Pat. Nos. 6,472,431; 6,780,889; 7,262,219; 7,851,506; 8,263,650; 8,324,275; and 8,772,302 each of which is incorporated herein by reference in its entirety).

Xyrem® is a commercially sold product comprised of 100% sodium oxybate (Na.GHB) and is approved for the treatment of excessive daytime sleepiness and cataplexy in patients with narcolepsy. Na.GHB has also been reported to be effective for relieving pain and improving function in patients with fibromyalgia syndrome, and in alleviating excessive daytime sleepiness and fatigue in patients with Parkinson's disease, improving myoclonus and essential tremor, and reducing tardive dyskinesia and bipolar disorder. See the references that are incorporated at the end of U.S. Pat. No. 6,472,431. Further, despite a general record of safety when used as prescribed, there are risks of abuse and misuse of Xyrem® which can cause serious medical problems, including seizures, loss of consciousness, coma, and death (see, e.g., FDA product label dated Nov. 13, 2006 for NDA no. 021196, which is incorporated by reference in its entirety).

Xyrem® for use with patients with narcolepsy, is a chronically used product which requires high levels of the drug. The amount of sodium intake from the drug significantly increases the daily sodium intake for patients, which is undesirable for patients with hypertension, heart disease, renal disease or at risk of stroke. Thus, there is a need for GHB formulations with lower sodium, such as those provided herein, particularly for patients with hypertension, heart disease, renal disease or at risk of stroke, yet provide additional health benefits from the presence of the other salts.

However, the therapeutic dose of 71.4 mEq/day (9 g sodium oxybate) is sufficiently high that shifting from sodium to another cation can push limits on acceptable daily intake of other cations and potentially cause other problems for certain patients. For example, potassium has poor tolerability in solution at high doses given on an empty stomach and can also be problematic for patients with kidney impairment. Therefore, formulations which reduce or eliminate sodium without exceeding levels of concern for other cations are particularly desirable.

Xyrem® is provided as an oral solution consisting of 500 mg/mL sodium oxybate (Na.GHB) that is pH adjusted with malic acid. Xyrem® is rapidly and well absorbed when given on an empty stomach. The absolute bioavailability for 2.25 g and 4.45 g sodium oxybate doses, relative to IV administration, is 88%. See the Xyrem® Product Insert. As a result, sodium oxybate is generally considered to be a high solubility, high permeability drug. (See Yu et al., *Pharm. Res.* 19 (7) 921-925). As such, for alternative formulations of GHB, such as those comprising cations other than sodium, but having comparable solubility, bioequivalence might be expected and a pharmacokinetic evaluation waived. See 21 CFR Part 320.22 Subpart B paragraph b(3).

However, as disclosed herein, despite the apparently rapid absorption of sodium oxybate, its presentation as an aqueous solution, and the absence of any other ingredients that would be expected to modify absorption behavior, formulations having the same GHB concentration do not display pharmacokinetics equivalent to Xyrem®. Furthermore, as also disclosed herein, the pharmacokinetic behavior of such formulations appears to depend on the amount of sodium and/or other cations present, as well as the amount of water in the formulation. Accordingly, one object of the present disclosure is to provide alternative formulations of GHB which are bioequivalent to Xyrem®. Provided herein are such alternative formulations which surprisingly display the desired bioequivalence.

The following patents and applications referred to throughout the application are hereby incorporated by reference in their entireties for all purposes, including the following: U.S. Pat. Nos. 6,472,431; 7,895,059; 8,461,197; 8,591,922; 8,759,394; 8,771,735; 8,772,306; 8,778,301 8,778,398; 8,952,029; and 9,050,302; and U.S. Publication No. 2012/0076865.

Objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

6.1 Definitions

As used herein, the term "gamma-hydroxybutyrate" (GHB) or "oxybate" refers to the negatively charged or anionic form (conjugate base) of gamma-hydroxybutyric acid. Without being limited by theory, GHB is believed to have the following structure:

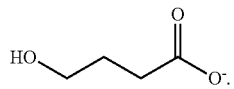

As used herein, the term "gamma-hydroxybutyric acid" refers to the protonated form (conjugate acid) of gamma-hydroxybutyrate. Without being limited by theory, gamma-hydroxybutyric acid is believed to have the following structure:

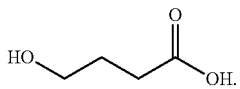

As used herein, the terms "sodium gamma-hydroxybutyrate" (Na.GHB) or "sodium oxybate" (Na.oxybate) refers to the sodium salt form of gamma-hydroxybutyric acid having the molecular weight of 126.09. Without being limited by any theory, Na.GHB is believed to have the following structure:

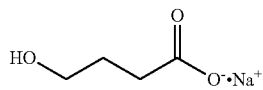

As used herein, the term "potassium gamma-hydroxybutyrate" (K.GHB) or "potassium oxybate" (K.oxybate) refers to the potassium salt form of gamma-hydroxybutyric acid having the molecular weight of 142.19. Without being limited by any theory, K.GHB is believed to have the following structure:

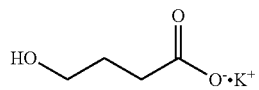

As used herein, the term "magnesium gamma-hydroxybutyrate" ($Mg.(GHB)_2$) or "magnesium oxybate" (Mg.oxybate) refers to the magnesium salt form of gamma-hydroxybutyric acid having the molecular weight of 230.50. Without being limited by theory, $Mg.(GHB)_2$ is believed to have the following structure:

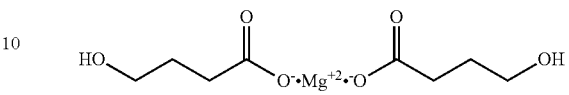

As used herein, the term "calcium gamma-hydroxybutyrate" ($Ca.(GHB)_2$) or "calcium oxybate" (Ca.oxybate) refers to the calcium salt form of gamma-hydroxybutyric acid having the molecular weight of 246.27. Without being limited by theory, $Ca.(GHB)_2$ is believed to have the following structure:

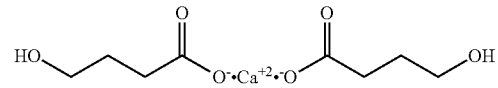

As used herein, the term "gamma-butyrolactone" (GBL) refers to a colorless oily liquid. Without being limited by theory, GBL is believed to have the following structure:

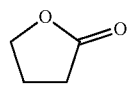

As used herein, the term "patient" refers to a mammal, particularly a human.

The terms "treat," "treating" or "treatment," as used herein, refer to a method of alleviating or abrogating a disease and/or its attendant symptoms.

As used herein, the term "about" or "approximately" means an acceptable error for a particular value as determined by those skilled in the art, which depends in part on how the value is measured or determined. In certain embodiments, the term "about" or "approximately" means within 10%, 9%, 8%, 7%, 6%, 5%, 4%, 3%, 2%, 1%, 0.5%, or 0.05% of a given value.

The term "substantial amount" shall mean over 1%.

By "pharmaceutically acceptable" it is meant the active ingredient, cation, salt, diluent, excipient or carrier must be compatible with the other ingredients of the formulation and not unduly deleterious, for example, that the active ingredient, cation, salt, diluent, excipient or carrier does not produce an adverse, allergic or other untoward reaction, when administered to an animal, or a human, as appropriate.

The term "salt" or "salts," as used herein, refers to a compound formed by the interaction of an acid and a base, the hydrogen atoms of the acid being replaced by the positive ion or cation of the base. Pharmaceutically acceptable salts, include inorganic acids such as, for example, hydrochloric or phosphoric acids, or such organic acids as malic, acetic, oxalic, tartaric, mandelic, and the like. Salts formed can also be derived from inorganic bases such as, for example, sodium, potassium, silicates, ammonium, calcium, or ferric hydroxides, and such organic bases as isopropylamine, trimethylamine, histidine, procaine and the like. In certain preferred embodiments, the salt is formed from an inorganic base that is a metal, for example, an alkali metal, such as lithium, potassium, sodium, or the like, an alkaline earth metal, such as magnesium, calcium, barium, or the like, or aluminum or zinc. Other salts may comprise ammonium. Alkali metals, such as lithium, potassium, sodium, and the like, may be used, preferably with an acid to form a pH adjusting agent. Examples of pharmaceutically acceptable base addition salts include those derived from inorganic bases like sodium hydroxide, potassium hydroxide, magnesium hydroxide, calcium hydroxide, or ammonium hydroxide, and the like (See, e.g., Berge et al., 1977, J. Pharm. Sci. 66: 1).

As used herein, the terms "salt of GHB" or "salts of GHB," as used herein, refer to a compound formed by the interaction of gamma-hydroxybutyric acid (the conjugate acid of GHB) with a base, for example, NaOH, KOH, $Mg(OH)_2$, and $Ca(OH)_2$, and the like, the hydrogen atoms of the acid being replaced by the positive ion or cation of the base. Such salts may include, for example, Na.GHB, K.GHB, $Mg.(GHB)_2$, and $Ca.(GHB)_2$, and the like. It will be understood by those skilled in the art that such salts may be in solid form, or such salts may be in partially or fully solvated form, for example, as when dissolved in an aqueous medium. It will be further understood by those skilled in the art, that, depending on the solubility of the salt in the aqueous medium, that the salt may be present in the aqueous medium as solvated cation(s) and anion(s), or as a precipitated solid, as illustrated below for the solubility equilibrium of $Ca.(GHB)_2$:

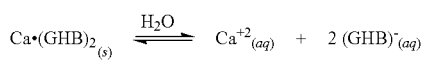

The terms "mixture of salts" or "salt mixture," as used herein, refers to salts of GHB where two or more different cations are present in combination with each other in a composition. Such mixtures of salts may include, for example, two or more salts selected from the group consisting of Na.GHB, K.GHB, $Mg.(GHB)_2$, and $Ca.(GHB)_2$.

Xyrem® contains 500 mg/mL Na.GHB. When referring to a mixture of GHB salts with different cations, the concentration in mg/mL will vary between formulations and/or pharmaceutical compositions of the same GHB strength. As used herein, a GHB concentration of 409 mg/mL is equivalent to the GHB content in 500 mg/mL of Na.GHB.

The term "wt/wt %," are used herein, refers to the normalized weight percent of a particular salt in a salt mixture. A sample calculation of wt/wt % is provided in Example 1 of the present disclosure.

The term "wt/wt % ratio," as used herein, refers to the ratio of wt/wt % values in a mixture of salt. For example, where the salts Na.GHB, K.GHB, $Mg.(GHB)_2$, and $Ca.(GHB)_2$ are present in a wt/wt %'s of 8%, 32%, 20% and 40%, respectively, the wt/wt % ratio of Na.GHB, K.GHB, $Mg.(GHB)_2$, and $Ca.(GHB)_2$ in the mixture is 8%:32%:20%:40%.

The terms "% molar equivalents" and "% mol. equiv.," as used herein, refer to molar composition of salts expressed as a percent of GHB (or "oxybate") equivalents. For example, formulations and/or pharmaceutical compositions as described herein comprise mixtures with varying percentages of oxybate, expressed as % molar equivalents (% mol. equiv.) of Na.GHB, K.GHB, $Mg.(GHB)_2$, and $Ca.(GHB)_2$. Those skilled in the art will understand that as each GHB unit is considered to be one molar equivalent, the monovalent cations, $Na^+$ and $K^+$, have one molar equivalent per salt, and the divalent cations, $Mg^{+2}$ and $Ca^{+2}$, have two molar equivalents per salt. A sample calculation of % mol. equiv. is provided in the Examples of the present disclosure. For convenience in comparing various salt compositions at the same oxybate molar dose, compositions expressed as percentages in this application refer to molar equivalent percentage (% molar equivalents) of each oxybate salt. This is usually close to, but not the same as, the composition that would be expressed as wt/wt %.

The term, "buffering agent," as used herein, refers to a weak acid or base used to maintain the pH of a solution near a chosen pH value after the addition of another acidic or basic compound. The function of such an agent is to prevent the change in pH when acids or bases are added to a solution. Such agents may be acids, bases, or combinations thereof.

The term, "adjusting agent," as used herein, refers to an acid or base used to alter the pH of a solution to a chosen pH value. The function of such an agent is to alter the pH of a solution to the desired value subsequent to the addition of acidic or basic compounds.

The term, "acid," as used herein, refers to a substance which accepts a share in a pair of electrons. Such substances include malic acid, citric acid, acetic acid, boric acid, lactic acid, hydrochloric acid, phosphoric acid, sulfuric acid, sulfonic acid, nitric acid, and the like.

The term, "base," as used herein, refers to a substance which shares a pair of electrons. Such substances include sodium hydroxide, potassium hydroxide, magnesium hydroxide, calcium hydroxide, and the like.

The term, "chemically stable," as used herein, refers to a chemical compound which is not particularly reactive in a specific environment and retains its useful properties on a timescale of its expected usefulness. Specifically, the usefulness of the compound is maintained in the presence of air, moisture, or heat. Conversely, the compound lacks chemical stability if it decomposes under the conditions of a specific environment. As used herein in certain embodiments, "chemically stable" may mean resistant to degradation of GHB into its known or unknown decomposition elements. The level of GBL that is acceptable can be up to 0.15% of the formulation as per the ICH guidelines for shelf-life determination.

The term, "microbial," as used herein, refers to a microscopic organism that comprises either a single cell, cell cluster or multicellular organism.

The term "resistant to microbial growth" or "resistant to microbial challenge," as used herein, means that the compositions or formulations meet the criteria set by the Food and Drug Administration and the U.S. Pharmacopoeia for products made with aqueous bases or vehicles, which for bacteria means not less than a 1.0 log reduction from the initial count at 14 days, and no increase from the 14 days count at 28 days, and for yeast and molds, no increase from the initial calculated count at 14 and 28 days.

The term, "preservative," as used herein, refers to a naturally occurring or synthetically produced substance which can be added to food, pharmaceuticals, paints, biological samples, wood, etc. to prevent decomposition by microbial growth or by chemical decomposition.

The term, "formulation," as used herein, refers to a stable and pharmaceutically acceptable preparation of a pharmaceutical composition disclosed herein.

The term, "liquid formulation," as used herein, refers to a water-based formulation, in particular, a formulation that is an aqueous solution.

The term, "low volume" or "low aqueous volume" or "reduced volume," as used herein, refers to an aqueous solution of about 100 mL or less.

The term, "volume of administration" as used here, refers to the volume of aqueous material used to ingest or swallow the formulations and/or pharmaceutical compositions comprising the GHB salts, as disclosed herein, including before or immediately after the formulations and/or pharmaceutical compositions are ingested or swallowed. This amount can, for example, include the formulations and/or pharmaceutical disclosed herein and any additional aqueous material used to dilute, wash down or chase the formulations and/or pharmaceutical compositions. The additional aqueous material includes for example, water and flavored beverages.

The term, "eating" as used herein, refers to ingesting or consuming calories and/or nutrients by way of solid or liquid food substances.

The term, "cataplexy," as used herein, refers to a condition where a patient exhibits a sudden and transient loss of muscle tone, often triggered by emotions.

The term, "daytime sleepiness," as used herein, refers to a condition where a patient exhibits persistent sleepiness, and often a general lack of energy, even after apparent adequate night time sleep.

The term, "narcolepsy," as used herein, refers to a chronic sleep disorder characterized by excessive sleepiness and sleep attacks at inappropriate times.

The term, "apnea," as used herein, refers to a condition where a patient suspends external breathing.

The term, "sleep time disturbances," as used herein, refers to a condition where a patient exhibits abnormal sleep patterns. Sleep time disturbances can be serious enough to interfere with normal physical, mental and emotional functioning.

The term, "sleep paralysis," as used herein, refers to a condition in which a patient who is falling asleep or awakening form sleep experience an inability to move. It is a transition state between wakefulness and rest characterized by complete muscle weakness.

The term, "hypnagogic hallucination," as used herein, refers to a transition state between wakefulness and sleep where a patient experiences vivid hallucinations.

The term, "sleep arousal," as used herein, refers to a condition where a patient engages in sexual acts while still asleep.

The term, "insomnia," as used herein, refers to a condition where a patient has difficulties falling asleep and maintaining sleep.

The term, "nocturnal myoclonus," as used herein, refers to a condition where a patient has repetitive movement of the limbs during sleep or even wakefulness which is sometimes confused with a seizure.

The term "flavoring" or "flavoring agent," as used herein, refers to a substance that alters the flavor of the composition during oral consumption. A type of "flavoring agent" would be a sweetener.

The term "coloring" or "coloring agent," as used herein, refers to a substance that alters the color of the composition.

The term "bioequivalent", as used herein, describes a formulation and/or pharmaceutical composition that is therapeutically equivalent to a reference product (e.g. Xyrem®) when given under the same conditions in a pharmacokinetic evaluation conforming to FDA Guidance on Bioequivalence Testing; regardless of biopharmaceutical class. A value that is "bioequivalent", as used herein, is meant to refer to a pharmacokinetic value (such as the Cmax or AUC of a formulation described herein) that exhibits substantially similar pharmacokinetic profiles or therapeutic effects. Bioequivalence may be demonstrated through several in vivo and in vitro methods. These methods may include, for example, pharmacokinetic, pharmacodynamic, clinical and in vitro studies. In some embodiments, bioequivalence may be demonstrated using any suitable pharmacokinetic measures or combination of pharmacokinetic measures known in the art, including loading dose, steady-state dose, initial or steady-state concentration of drug, biological half-life, elimination rate, area under the curve (AUC), clearance, the peak blood or plasma concentration (Cmax), time to peak concentration (Tmax), bioavailability and potency. In some embodiments, a value is bioequivalent to a reference pharmacokinetic value when the geometric mean of the AUC and/or the Cmax is between 80% and 125% (e.g., at 90% confidence interval) of the reference pharmacokinetic value.

In some embodiments, a pharmaceutical composition is bioequivalent to a reference pharmaceutical composition when the pharmaceutical composition produces an average Cmax and/or AUC that is substantially the same as the Cmax and/or AUC of the reference pharmaceutical composition when administered under the same conditions. In some embodiments, a pharmaceutical composition is bioequivalent to a reference pharmaceutical composition when the pharmaceutical composition produces a Cmax and/or AUC that is within 80% and 125% of the Cmax and/or AUC of the reference pharmaceutical composition when administered under the same condition. For example, a pharmaceutical composition is bioequivalent to Xyrem® when the pharmaceutical composition produces an average Cmax and/AUC is between 80% and 125% of the Cmax and/or AUC of Xyrem® when administered under the same conditions.

The expression "consists essentially of" as used herein, means that specific further components can be present in a mixture or composition, namely those not materially affecting the essential characteristics of the mixture or composition.

6.2 Pharmaceutical Compositions Comprising Salt Mixtures of GHB

In certain aspects, provided herein are pharmaceutical compositions comprising gamma-hydroxybutyrate (GHB) and one or more pharmaceutically acceptable cations of an alkali metal or an alkaline earth metal. As used herein, "alkali metal" means any of the elements found in Group IA of the periodic table, including, for example, lithium, sodium, and potassium. As used herein, "alkaline earth metal" means any of the elements found in Group II of the periodic table, including, for example, magnesium and calcium.

In certain embodiments, the pharmaceutical compositions comprise GHB and more than one pharmaceutically acceptable cations of an alkali metal or an alkaline earth metal.

In certain embodiments, the pharmaceutical compositions comprise GHB and more than one (two or more) cations selected from the group consisting of $Na^+$, $K^+$, $Mg^{+2}$, and $Ca^{+2}$. In certain embodiments, the pharmaceutical compositions comprise GHB and all three cations selected from the group consisting of $Na^+$, $K^+$, and $Ca^{+2}$. In certain embodiments, the pharmaceutical compositions comprise less than 100% of the cation $Na^+$, so as to minimize the amount of sodium, particularly in patients with hypertension, heart disease, renal disease or at risk of stroke or to improve the taste of the compositions. In certain embodiments, the pharmaceutical compositions comprise from about 50% to about 80% of the cation Na⁺. In other embodiments, the pharmaceutical compositions comprise from about 0% to about 40% of the cation Na⁺. Each embodiment has a different advantage.

In certain aspects, provided herein are pharmaceutical compositions comprising salts of GHB. As used herein, the term "salt of GHB" or "salts of GHB" is used interchangeably with the term "cation." For example, a pharmaceutical composition comprising GHB and the four cations Na⁺, K⁺, Mg⁺², and Ca⁺² will be understood by those skilled in the art to also mean a pharmaceutical composition comprising the salts Na.GHB, K.GHB, Mg.(GHB)₂, and Ca.(GHB)₂. It will be also understood by those skilled in the art that such salts may be in solid form, or may be in partially or fully solvated form, for example, as when dissolved in an aqueous medium. It will be further understood by those skilled in the art, that, depending on the solubility of the salt in the aqueous medium, that the salt may be present in the aqueous medium as solvated cation(s) and anion(s), or as a precipitated solid.

In certain embodiments, the pharmaceutical composition comprises a mixture of two or more GHB salts, wherein the mixture comprises Na.GHB, and further comprises any one of the salts selected from the group consisting of K.GHB, Mg.(GHB)₂, and Ca.(GHB)₂. In certain embodiments, the pharmaceutical composition comprises Na.GHB, K.GHB, and Ca.(GHB)₂. In certain embodiments, the pharmaceutical composition comprises Na.GHB, and Ca.(GHB)₂. In certain embodiments, the pharmaceutical composition comprises Na.GHB, Mg.(GHB)₂, and Ca.(GHB)₂. In certain embodiments, the pharmaceutical composition comprises Na.GHB and K.GHB. In certain embodiments, the pharmaceutical composition comprises Na.GHB, K.GHB, and Mg.(GHB)₂.

In certain embodiments, the pharmaceutical composition comprises Na.GHB and Mg.(GHB)₂.

The amounts of the cations below are described in various ranges. The cations can be present in the ranges found in U.S. Pat. Nos. 8,591,922; 8,901,173; and 9,132,107.

In certain embodiments, the Na.GHB salt is present in the mixture in a percentage of at least 50%. In certain embodiments, the Na.GHB salt is present in about 50% to about 80%. In certain embodiments, the Na.GHB salt is present in about 50% to about 70%. In certain embodiments, the Na.GHB salt is present in about 50% to about 60%. In certain embodiments, the Na.GHB salt is present in about 50% to about 55%. In certain embodiments, the Na.GHB salt is present between 40% and 50% and in others between 5% to 45%. In certain embodiments, the Na.GHB salt is present in about 5% to 35%. In certain embodiments, the Na.GHB salt is present in about 5% to 25%. In certain embodiments, the Na.GHB salt is present in about 5% to 10%.

In certain embodiments, the mixture comprises between 40% and 50% Na.GHB, and in others between 45% and 50% Na.GHB. In certain embodiments, the mixture comprises about 5% to 45% Na.GHB.

In certain embodiments, the mixture comprises at least 50% Na.GHB. In certain embodiments, the mixture comprises about 50% to about 80% Na.GHB. In certain embodiments, the mixture comprises about 50% to about 70% Na.GHB. In certain embodiments, the mixture comprises about 50% to about 60% Na.GHB. In certain embodiments, the mixture comprises about 50% to about 55% Na.GHB. In certain embodiments, the mixture comprises between 40% and 50% Na.GHB, and in others between 5% to 45% Na.GHB. In certain embodiments, the mixture comprises about 5% to 35% Na.GHB. In certain embodiments, the mixture comprises about 5% to 25% Na.GHB. In certain embodiments, the mixture comprises about 5% to 10% Na.GHB.

In certain embodiments, the mixture comprises between 40% and 50% Na.GHB, and in others between 45% and 50% Na.GHB. In certain embodiments, the mixture comprises about 5% to 45% Na.GHB.

In certain embodiments, the remaining one, two or three or more cations that are present in the mixture in amounts to make up the remainder of the cations in the formulation and/or pharmaceutical composition. The amount of each depends on the amount of Na⁺ and the amount of other cations. For example, if Na⁺ is present at 50% and Ca⁺² and K⁺ are also present, then Ca⁺² and K⁺ can each be present in varying amount from 5-40% to add up to the remaining 50%. If Mg⁺² is also present in the mixture then the non-sodium component 50% is divided three ways. In some embodiments, the mixture does not comprise a significant amount of Mg.(GHB)₂ or Ca.(GHB)₂, and therefore the formulation and/or pharmaceutical composition does not have a significant amount of Mg.(GHB)₂ or Ca.(GHB)₂. Care can be taken to adjust any specific cation concentration to levels that are acceptable to patients. It may not be preferred to add any cation to a level that might be disadvantageous to patients generally. For example, potassium has poor tolerability in solution at high doses given on an empty stomach and can also be a problem for patients with kidney impairment.

In certain embodiments, Na⁺ is present at 50% and Ca²⁺ and K⁺ are also present, then Ca²⁺ and K⁺ can each be present in varying amount from 5-45% to add up to the remaining 50%.

In certain embodiments, the K.GHB, Mg.(GHB)₂ or Ca.(GHB)₂ salt is present in the mixture at about 1% to about 5%, about 5% to about 10%, about 10% to about 15%, about 15% to about 20%, about 20% to about 25%, about 25% to about 30%, about 30% to about 35%, or about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In certain embodiments, the K.GHB, Mg.(GHB)₂ or the Ca.(GHB)₂ salt is absent.

In certain embodiments, the mixture comprises K.GHB, Mg.(GHB)₂ or the Ca.(GHB)₂ in about 1% to about 5%, about 5% to about 10%, about 10% to about 15%, about 15% to about 20%, about 20% to about 25%, about 25% to about 30%, about 30% to about 35%, or about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In certain embodiments, the mixture comprises about 0% K.GHB. In certain embodiments, the mixture comprises about 0% Mg.(GHB)₂. In certain embodiments, the mixture comprises about 0% Ca.(GHB)₂.

In certain embodiments, the mixture comprises K.GHB in about 1% to about 5%, about 5% to about 10%, about 10% to about 15%, about 15% to about 20%, about 20% to about 25%, about 25% to about 30%, about 30% to about 35%, or about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In certain embodiments, the mixture comprises about 0% K.GHB.

In certain embodiments, the mixture comprises Mg.(GHB)$_2$ in about 1% to about 5%, about 5% to about 10%, about 10% to about 15%, about 15% to about 20%, about 20% to about 25%, about 25% to about 30%, about 30% to about 35%, or about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In certain embodiments, the mixture comprises about 0% Mg.(GHB)$_2$.

In certain embodiments, the mixture comprises Ca.(GHB)$_2$ in about 1% to about 5%, about 5% to about 10%, about 10% to about 15%, about 15% to about 20%, about 20% to about 25%, about 25% to about 30%, about 30% to about 35%, or about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 100%. In certain embodiments, the mixture comprises about 0% Ca.(GHB)$_2$.

In certain embodiments, the pharmaceutical composition has reduced sodium compared to Xyrem®, wherein the Na.GHB salt is present in the mixture at about 50% to about 80%.

In certain embodiments, the pharmaceutical composition comprises a mixture of two or more GHB salts, wherein the mixture comprises at least 50% of a sodium salt of Na.GHB, and further comprises one or more of the following salts, K.GHB, Ca.(GHB)$_2$ and Mg.(GHB)$_2$. In certain embodiments, the Na.GHB salt is present in the mixture at about 50% to 80%. In certain embodiments, the Na.GHB salt is present in the mixture at about 50% to 70%. In certain embodiments, the Na.GHB salt is present in the mixture at about 50% to 60%. In certain embodiments, the Na.GHB salt is present in the mixture at about 50% to 55%.

In certain embodiments, the pharmaceutical composition comprises a mixture of two or more salts of GHB, wherein the mixture comprises of at least 50% of Na.GHB and further comprises one or more of K.GHB and Ca.(GHB)$_2$.

In certain embodiments, the pharmaceutical composition comprises a mixture of two or more salts of GHB, wherein the mixture consists essentially of at least 50% of Na.GHB and one or more of K.GHB and Ca.(GHB)$_2$.

In certain embodiments, the pharmaceutical composition comprises a mixture of three or more salts of GHB.

In certain embodiments, the pharmaceutical composition does not comprise a substantial amount of Mg.(GHB)$_2$ or Ca.(GHB)$_2$. In certain embodiments, the mixture does not comprise a substantial amount of Mg.(GHB)$_2$ or Ca.(GHB)$_2$. In certain embodiments, the mixture consists of 50% to 80% Na.GHB, at least 10% K.GHB, and at least 10% Ca.(GHB)$_2$.

In certain embodiments, the composition comprises a mixture of three or more salts of GHB, wherein the mixture comprises between 50% to 80% Na.GHB, between 30% to 40% K.GHB, and between 10% to 20% Ca.(GHB)$_2$. In certain embodiments, the mixture comprises between 50% to 80% Na.GHB, between 10% to 40% K.GHB, and between 10% to 20% Ca.(GHB)$_2$.

In certain embodiments, the composition comprises a mixture of three or more salts of GHB, wherein the mixture consists essentially of between 50% to 80% Na.GHB, between 10% to 40% K.GHB, and between 10% to 20% Ca.(GHB)$_2$.

In certain embodiments, the composition comprises a mixture of three or more salts of GHB, wherein the mixture comprises about 50% to 80% Na.GHB, about 30% to 40% K.GHB, and about 10% to 20% Ca.(GHB)$_2$. In certain embodiments, the mixture comprises about 50% to 80% Na.GHB, about 10% to 40% K.GHB, and about 10% to 20% Ca.(GHB)$_2$.

In certain embodiments, the composition comprises a mixture of three or more salts of GHB, wherein the mixture consists essentially of about 50% to 80% Na.GHB, about 10% to 40% K.GHB, and about 10% to 20% Ca.(GHB)$_2$.

In certain embodiments, the composition comprises a mixture of three or more salts of GHB, wherein the mixture comprises between about 50% to 80% Na.GHB, between about 30% to 40% K.GHB, and between about 10% to 20% Ca.(GHB)$_2$. In certain embodiments, the mixture comprises between about 50% to 80% Na.GHB, between about 10% to 40% K.GHB, and between about 10% to 20% Ca.(GHB)$_2$.

In certain embodiments, the composition comprises a mixture of three or more salts of GHB, wherein the mixture consists essentially of between about 50% to 80% Na.GHB, between about 10% to 40% K.GHB, and between about 10% and 20% Ca.(GHB)$_2$.

In certain embodiments, the composition comprises a mixture of three or more salts of GHB, wherein the mixture comprises between 50% and 60% Na.GHB, between 20% and 40% K.GHB, and between 10% and 20% Ca.(GHB)$_2$. In certain embodiments, the mixture comprises between 50% and 60% Na.GHB, between 10% and 40% K.GHB, and between 10% and 20% Ca.(GHB)$_2$.

In certain embodiments, the composition comprises a mixture of three or more salts of GHB, wherein the mixture comprises about 50% to about 60% Na.GHB, about 20% to about 40% K.GHB, and about 10% to about 20% Ca.(GHB)$_2$. In certain embodiments, the mixture comprises about 50% to 60% Na.GHB, about 10% to 40% K.GHB, and about 10% to 20% Ca.(GHB)$_2$.

In certain embodiments, the composition comprises a mixture of three or more salts of GHB, wherein the mixture comprises between about 50% and about 60% Na.GHB, between about 20% and about 40% K.GHB, and between about 10% and about 20% Ca.(GHB)$_2$. In certain embodiments, the mixture comprises between about 50% and about 60% Na.GHB, between about 10% and about 40% K.GHB, and between about 10% and about 20% Ca.(GHB)$_2$.

In certain embodiments the mixture comprises 45% to 55% Na.GHB, 30% to 40% K.GHB, and 10% to 20% Ca.(GHB)$_2$. In certain embodiments the mixture comprises 48% to 52% Na.GHB, 32% to 36% K.GHB, and 14% to 18% Ca.(GHB)$_2$. In certain embodiments, the mixture does not have a substantial amount of Mg.(GHB)$_2$. In other embodiments, the mixture does not have a substantial amount of Ca.(GHB)$_2$.

In certain embodiments, the pharmaceutical composition comprises a mixture of three GHB salts, wherein the mixture comprises at least 50% Na.GHB, and further comprises K.GHB and Ca.(GHB)$_2$, In certain embodiments, the mixture comprises between 50% and 60% of Na.GHB, between 10% and 40% K.GHB, and between 10% and 20% Ca.(GHB)$_2$.

In certain embodiments, the pharmaceutical composition does not comprise a substantial amount of Mg.(GHB)$_2$. In certain embodiments, the mixture does not comprise a substantial amount of Mg.(GHB)$_2$. In certain embodiments, the Na.GHB, K.GHB, and Ca.(GHB)$_2$ salts are present in the mixture in a ratio of about 50%:34%:16%.

In certain embodiments, the pharmaceutical composition of GHB comprising less than 100 mL of an aqueous solution, wherein the aqueous solution comprises a mixture of two or more salts of GHB, the mixture comprising between 40% and 50% Na.GHB, and further comprising one or more salts selected from K.GHB, Ca.(GHB)$_2$, and Mg.(GHB)$_2$.

In certain embodiments, the mixture comprises about 40% to about 50% Na.GHB, and further comprising one or more salts selected from K.GHB, Ca.(GHB)$_2$, and Mg.(GHB)$_2$. In certain embodiments, the mixture comprises between about 40% and about 50% Na.GHB, and further comprising one or more salts selected from K.GHB, Ca.(GHB)$_2$, and Mg.(GHB)$_2$.

In certain embodiments, the pharmaceutical composition of GHB comprising less than 100 mL of an aqueous solution, wherein the aqueous solution comprises a mixture of two or more salts of GHB, the mixture essentially consists of about 40% to about 50% Na.GHB, and further comprising one or more salts selected from K.GHB, Ca.(GHB)$_2$, and Mg. (GHB)$_2$.

In certain embodiments, the pharmaceutical composition comprises a mixture which contains between 40% and 50% Na.GHB, wherein the composition is provided to the patient in an aqueous solution of between 25 and 100 mL. In certain embodiments, the pharmaceutical composition comprises the mixture dissolved or dispersed in an aqueous solution of between 40 and 75 mL. In certain embodiments, the pharmaceutical composition comprises the mixture dissolved or dispersed in an aqueous solution of between 55 and 65 mL.

In certain embodiments, the aqueous solution has a volume of about 25 mL to about 100 mL. In certain embodiments, the aqueous solution has a volume of about 40 mL to about 75 mL. In certain embodiments, the aqueous solution has a volume of about 55 mL to about 65 mL. In certain embodiments, the aqueous solution has a volume of about 60 mL.

In certain embodiments, the pharmaceutical composition comprises the mixture dissolved or dispersed in an aqueous solution of between 25 and 75 mL. In certain embodiments, the pharmaceutical composition comprises about 60 mL of an aqueous solution.

In certain embodiments, the pharmaceutical composition comprises between 25 and 100 mL of an aqueous solution. In certain embodiments the pharmaceutical composition comprises between 40 and 75 mL of an aqueous solution. In certain embodiments the pharmaceutical composition comprises between 55 and 65 mL of an aqueous solution.

In certain embodiments the pharmaceutical composition is an aqueous solution having a volume of about 25 mL to about 100 mL. In certain embodiments the pharmaceutical composition is an aqueous solution having a volume of about 40 mL to about 75 mL. In certain embodiments the pharmaceutical composition is an aqueous solution having a volume of about 55 mL to about 65 mL.

In certain embodiments, the pharmaceutical composition is bioequivalent to Xyrem® which is Na.GHB. In certain embodiments, the pharmaceutical composition produces an average maximum GHB plasma concentration (Cmax) that is substantially the same as the Cmax of Na.GHB. In certain embodiments, the pharmaceutical composition produces a Cmax that is within 80% and 125% of the Cmax of Na.GHB. In certain embodiments, the pharmaceutical composition produces an average maximum GHB plasma area under the curve (AUC) and Cmax that is substantially the same as Na.GHB. In certain embodiments, the pharmaceutical composition produces an AUC that is between 80% and 125% of the AUC of Na.GHB.

In certain embodiments, the pharmaceutical composition is bioequivalent to a pharmaceutical composition comprising about 100% Na.GHB when administered to a patient.

In certain embodiments, the average maximum GHB plasma concentration (Cmax) is within 10% of the Cmax of a pharmaceutical composition comprising about the same amount of 100% Na.GHB when administered to a patient. In certain embodiments, the AUC is within 10% of the AUC of a pharmaceutical composition comprising about the same amount of 100% Na.GHB when administered to a patient.

In certain embodiments, the pharmaceutical composition is formulated as a liquid formulation, wherein the Na.GHB salt is present at less than 40%. In these embodiments, the pharmaceutical composition is more resistant to a food effect and has a lower Cmax compared to Na.GHB.

In certain embodiments, the pharmaceutical composition comprises a mixture of two or more GHB salts, wherein the mixture comprises less than 40% Na.GHB, and further comprises one or more of the following salts, K.GHB, Ca.(GHB)$_2$ and Mg.(GHB)$_2$. In certain embodiments, the Na.GHB salt is present in the mixture at about 0% to 30%. In certain embodiments, the Na.GHB salt is present in the mixture at about 5% to 25%. In certain embodiments, the Na.GHB salt is present in the mixture at about 5% to 10%.

In certain embodiments, the pharmaceutical composition comprises a mixture of three or more GHB salts, wherein the mixture comprises at least 10% K.GHB, at least 10% Ca.(GHB)$_2$ and at least 10% Mg.(GHB)$_2$. In certain embodiments, the pharmaceutical composition comprises a mixture of two or three GHB salts, in addition to Na.GHB, wherein the mixture further comprises 20 to 80%, K.GHB, Ca.(GHB)$_2$ or Mg.(GHB)$_2$. In certain embodiments, the pharmaceutical composition comprises a mixture of three or more GHB salts, wherein the mixture comprises between 10 and 50% K.GHB, between 10 and 50% Ca.(GHB)$_2$ and between 10 and 50% Mg.(GHB)$_2$ for the non-sodium salts.

In certain embodiments, the Na.GHB, K.GHB, Mg.(GHB)$_2$, and Ca.(GHB)$_2$ salts are present in the mixture at a ratio of about 8%:23%:21%:48%, respectively.

6.2.1 Concentrations and pH Values

In certain embodiments, the pharmaceutical composition comprises an aqueous solution.

In certain embodiments, the concentration of the mixture of salts of GHB in the solution is about 250 mg/mL to about 750 mg/mL, about 350 mg/mL to about 650 mg/mL, about 400 mg/mL to about 600 mg/mL, about 450 mg/mL to about 550 mg/mL. In certain embodiments, the concentration of the mixture of salts of GHB in the solution is centered around 409 mg/mL GHB, which equates to 500 mg/mL Na.GHB. See U.S. Pat. No. 6,472,431, which is incorporated by reference in its entirety.

It will be understood that the maximum solubility of GHB is affected by the pH of the aqueous medium. For example, at about pH 4, the maximum amount of Na.GHB that can be dissolved is about 450 mg/mL. The value of pH that is conducive to GHB solubility increases so that the minimal pH that will dissolve 750 mg/mL GHB was found to be about pH 6.8.

Accordingly, in certain embodiments, the pharmaceutical composition has a pH of about 7.0 to about 9.0, about 7.0 to about 8.5, about 7.3 to about 8.5.

In certain embodiments, the pharmaceutical composition is chemically stable and resistant to microbial growth. In certain embodiments, the pharmaceutical composition is free of preservatives.

It will also be understood that the pH of the aqueous solution affects the resistance of the pharmaceutical composition to microbial growth at about 409 mg/mL GHB, which equates to, e.g., 500 mg/mL Na.GHB. For example, Na.GHB at this concentration (500 mg/mL) is resistant to microbial growth in an aqueous medium when the pH is between about pH 5 and pH 9. Compositions at about pH 6 to about pH 7.5 are particularly resistant to microbial growth. However, at concentrations of GHB greater than about 750 mg/mL above about pH 7.5, the resistance to microbial growth is reduced. See U.S. Pat. No. 6,472,431.

It will be further understood that the chemical stability of GHB is affected by pH. Accordingly, the method for preparing GHB, as described herein, particularly as disclosed in the specific examples, varies with pH. The impurity gamma butyrolactone (GBL) begins to form substantially if the pH is about 6 or less. Compositions with a pH of greater than about 6.0 are preferred to produce chemically stable formulations of GHB. Thus, a preferred range for chemically stable GHB would be from about pH 6 to about pH 9. However, any pH or range of pH values where a clinically acceptable amount of GBL is present is also contemplated as being preferred, and is encompassed by the present invention.

In certain embodiments, a pH adjusting or buffering agent may be added to the composition. The choice of a pH adjusting or buffering agent may affect the resistance to microbial challenge and/or the stability of GHB, as measured by the reduction in assayable GHB. Compositions of GHB, pH adjusted or buffered with malic or other acids are resistant to both microbial growth and chemical degradation of GHB, and are preferred. Other pH adjusting or buffering agents may be selected. Agents that adjust pH that are selected on this basis may undergo a taste testing study. However, any pH adjusting or buffering agent disclosed herein or as would be known to those skilled in the art is contemplated as being useful from the compositions or formulations disclosed herein. Of course, any salt, flavoring agent, excipient, or other pharmaceutically acceptable addition described herein, or as would be known to those skilled in the art, is contemplated as being useful for the compositions or formulations disclosed herein. See U.S. Pat. No. 6,472,431, and Remington, The Science and Practice of Pharmacy, 22nd Ed. 2013, each of which is hereby incorporated by reference in its entirety.

In certain embodiments, the pH adjusting or buffering agent is an acid. In certain embodiments, the pH adjusting or buffering agent is an inorganic acid or an organic acid. In certain embodiments, the pH adjusting or buffering agent is selected from the group consisting of malic acid, citric acid, acetic acid, boric acid, lactic acid, hydrochloric acid, phosphoric acid, sulfuric acid, sulfonic acid, and nitric acid. In certain embodiments, the pH adjusting or buffering agent is malic acid. See U.S. Pat. No. 6,472,431.

6.2.2 Formulations

The aqueous solutions disclosed herein typically comprise an effective amount of GHB, or a salt or mixture of salts of GHB as disclosed herein, which may be dissolved or dispersed in a pharmaceutically acceptable carrier and/or an aqueous medium.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Insofar as any conventional media or agent is incompatible with the active ingredient, its use in the therapeutic compositions is not appropriate. Supplementary compatible active ingredients can be incorporated into the compositions. For human administration, preparations should meet sterility, pyrogenicity, general safety and purity standards as required by the Food and Drug Administration (FDA). See Remington, The Science and Practice of Pharmacy, $22^{nd}$ Ed. 2013.

In certain embodiments, the compositions disclosed herein are provided in a formulation, preferably, a liquid formulation, although solid formulations are also contemplated. For any examples of excipients, colorants, flavorants, or other components of the formulation; see Remington, The Science and Practice of Pharmacy, $22^{nd}$ Ed. 2013.

In certain embodiments, the formulation is chemically stable and resistant to microbial growth. In certain embodiments, the formulation does not need, and may be free of preservatives. In certain embodiments, the level of gamma-butyrolactone (GBL) is 0.1% or less of the formulation. However, if preservatives are added they may include, but are not limited to, xylitol, sodium benzoate, methylparaben, propyl gallate BP, sorbic acid, chlorobutanol, dihydroacetic acid, monothioglycerol, potassium benzoate, propylparaben, benzoic acid, benzalkonium chloride, alcohol, benzoic acid, benzalkonium chloride, benzethonium chloride, benzyl alcohol, butylparaben, cetylpyridinium chloride, ethylenediamine, ethylparaben, ethyl vanillin, glycerin, hypophosphorus acid, methylparaben, phenol, phenylethyl alcohol, phenylmercuric nitrate, propylparaben, sassafras oil, sodium benzoate, sodium propionate, thimerosal and potassium sorbate. Preferred preservatives may be selected from the group comprising, but not limited to, xylitol, sodium benzoate, methylparaben, propylparaben and potassium sorbate. Xylitol is particularly preferred in certain compositions disclosed herein, because it acts as an preservative and a sweetener, is a caries preventative, is less laxative than other sweeteners, and is recommended for diabetics. See U.S. Pat. Nos. 8,324,275 and 8,952,062, and Remington, The Science and Practice of Pharmacy, $22^{nd}$ Ed. 2013, each of which is incorporated hereby by reference in its entirety.

In certain embodiments, the formulation is suitable for oral administration.

In certain embodiments, the formulation additionally comprises a flavoring agent. Preferred sweeteners or flavoring agents would be microbially non-metabolizable. Especially preferred sweeteners or flavoring agents would be carbohydrates such as xylitol and sorbitol. Such flavoring agents include, but are not limited to, acacia syrup, anethole, anise oil, aromatic elixir, benzaldehyde, benzaldehyde elixir-compound, caraway, caraway oil, cardamom oil, cardamom seed, cardamom spirit, cardamom tincture-compound, cherry juice, cherry syrup, cinnamon, cinnamon oil, cinnamon water, citric acid, citric acid syrup, clove oil, coca, coca syrup, coriander oil, dextrose, eriodictyon, eriodictyon fluidextract, eriodictyon syrup-aromatic, ethyl acetate, ethyl, vanillin, fennel oil, ginger, ginger fluidextract, ginger oleoresin, glucose, glycerin, glycyrrhiza, glycyrrhiza elixir, glycyrrhiza extract, glycyrrhiza extract-pure, glycyrrhiza fluidextract, glycyrrhiza syrup, honey, non-alcoholic elixir, lavender oil, citrus extract or oil, lemon oil, lemon tincture, mannitol, methyl salicylate, nutmeg oil, orange-bitter-elixir, orange-bitter-oil, orange flower oil, orange flower water, orange oil, orange peel-bitter, orange-peel-sweet-tincture, orange spirit-compound, compound, orange syrup, peppermint, peppermint oil, peppermint spirit, peppermint water, phenylethyl alcohol, raspberry juice, raspberry syrup, rosemary oil, rose oil, rose water, saccharin, saccharin calcium, saccharin sodium, sarsaparilla syrup, sorbitol solution, spearmint, spearmint oil, sucralose, sucrose, syrup, thyme oil, tolu balsam, tolu balsam syrup, vanilla, vanilla tincture, vanillin or wild cherry syrup.

In certain embodiments, the formulation additionally comprises a coloring agent. Preferred coloring agents would be microbially non-metabolizable.

In certain embodiments, the formulation is administered in a single or multiple dosage regimen.

Any of the above formulations may be prepared and/or packaged as a powdered or dry form for mixing with an aqueous medium before oral administration, or they may be prepared in an aqueous medium and packaged. After mixing with an aqueous medium, preferably to prepare a solution, these formulations are resistant to both microbial growth and chemical conversion of GHB to GBL, thereby increasing the shelf-life of therapeutic formulations of GHB, or salt or mixture of salts of GHB, in an aqueous medium. These formulations then provide an easily titratable liquid medium for measuring the dosage of GHB, or salt or mixture of salts of GHB, to be administered to a patient. Additional embodiments of the composition and methods of preparation are described below and in the examples.

In certain embodiments, especially with Na.GHB amounts between 40% and 50%, the formulation is present in a low volume of aqueous solution. As described herein, by "low volume" it is meant to include an aqueous solution of about 100 mL or less, including the aqueous medium and any wash or chase volume, for administration of a single GHB dose. Preferably the low volume is between about 25 mL to 75 mL, or between 55 mL to 65 mL of total aqueous volume given to the patient. In certain embodiments, for example, formulations with reduced sodium, the formulation requires less aqueous volume in order to be ingested, is more palatable, provides better patient compliance, is more tolerable, and/or is bioequivalent in comparison to GHB formulations of Na.GHB. It should be understood by those skilled in these arts that 25-100 mL (or about 1-3 ounces) of fluid is an acceptable amount of aqueous solvent to dilute the formulations disclosed herein, in order to ingest, improve taste, and/or "wash down" the GHB salts. For certain individuals, having a reduced-volume for administration offers an improved nightly dosing regimen which may alleviate unwanted side-effects associated with consuming liquids before bedtime, such as bed-wetting, restlessness and/or other sleep time disturbances.

The GHB, or salt or mixture of salts of GHB disclosed herein, may be lyophilized for more ready formulation into a desired vehicle or medium where appropriate. The GHB or salt(s) thereof may also be formulated for parenteral administration, e.g., formulated for injection via intravenous, intraarterial, intramuscular, sub-cutaneous, intralesional, intraperitoneal or other parenteral routes. The preparation of a pharmaceutical composition that comprises an aqueous solution that contains GHB or salt(s) thereof as an active component or ingredient will be known to those of skill in the art in light of the present disclosure. Typically, such compositions can be prepared as injectables, either as liquid solutions or suspensions. Solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including, e.g., aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free acid or pharmacologically acceptable salts can be prepared in water suitably mixed with hydroxypropyl cellulose and/or a pharmaceutically acceptable surfactant. Dispersions can also be prepared in glycerol, liquid polyethylene glycols, and mixtures thereof as well as in oils. Under ordinary conditions of storage and use, these preparations may contain a preservative to further prevent the growth of microorganisms.

The carrier can also be a solvent or dispersion medium containing, for example, water, ethanol, polyol (for example, glycerol, propylene glycol, and liquid polyethylene glycol, or the like), suitable mixtures thereof, and vegetable oils. The proper fluidity can be maintained, for example, by the use of a substance, such as lecithin (e.g., a coating), by the maintenance of the required particle size in the case of dispersion and by the use of surfactants. The prevention of the action of microorganisms can be brought about by any of the preservatives described herein, or as would be known to those skilled in the art, including various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate.

Sterile injectable solutions are prepared by incorporating the active compounds in the required amount in the appropriate solvent with, various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent (although DMSO may not now be a permitted human drug) is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of fluid or injected at the proposed site of infusion, (see, e.g., "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The GHB may be prepared in a formulation and/or pharmaceutical composition disclosed herein to comprise about 100 to about 10,000 milligrams per dose as administered to the patient. The typical dose range is approximately 4.5-9 g/day; see the Xyrem® Product Insert. Other dose ranges include 6-8 g/day multiple or single doses can be administered but it is typical to give two divided doses per day. The Xyrem® instructions recommend two equally divided doses.

In addition to the pharmaceutical compositions formulated for parenteral administration, such as intravenous or intramuscular injection, other pharmaceutically acceptable forms include, e.g., tablets or other solids; liposomal formulations; time release capsules, such as sustained or delayed release forms, including beads, pellets, or resins; and any other form currently used, including creams, which then may be admixed with an aqueous medium for oral administration.

One may also use nasal solutions or sprays, aerosols or inhalants in connection with the pharmaceutical compositions and/or formulations disclosed herein. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5, though other pH ranges disclosed herein the specific examples, such as pH 3 to about pH 9, or pH 6 to about 7.5, are contemplated. In addition, preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

The preferred oral formulations may include such normally employed excipients, as, for example, pharmaceutical grades of xylitol, mannitol, lactose, starch, magnesium stearate, sodium saccharin, cellulose, magnesium carbonate and the like. These compositions can take the form of solutions, suspensions, tablets, pills, capsules, sustained release formulations or powders to be admixed with an aqueous medium. In certain defined embodiments, oral pharmaceutical compositions will comprise an inert diluent or assimilable edible carrier, or they may be enclosed in hard or soft shell gelatin capsule, or they may be compressed into tablets, or the GHB or salt(s) thereof may be packaged separately from or in combination with the excipients, salts, flavorings or any other components described herein, to be admixed with an aqueous medium for oral or injectable formulations, or they may be incorporated directly with the food (i.e. a beverage) of the diet.

For oral therapeutic administration, the active compounds may be incorporated with excipients and used in the form of tablets, buccal tablets or tabs, troches, capsules, elixirs, suspensions, syrups, wafers, and the like, to be admixed with an aqueous medium. Such compositions and preparations should contain at least 0.1% of the active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, natural as gum tragacanth, acacia, cornstarch, or gelatin or synthetic as polyvinyl acetate; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a natural or synthetic flavoring agent. When the dosage unit form is a capsule for admixing with a specific volume of an aqueous medium, it may contain, in addition to materials of the above type, a liquid carrier. Various other materials may be present as coatings or to otherwise modify the physical form of the dosage unit. For instance, tablets, pills, or capsules may be coated with sugar, natural or synthetic polymers, or both. A syrup or elixir may contain the active compounds, sucrose as a sweetening agent, a preservative, a dye and/or a flavoring.

One embodiment of the formulations disclosed herein can be a solid with different release properties. One embodiment is a unit dosage form that is a tablet for immediate release comprising a relatively high weight-percentage of sodium oxybate, in combination with a relatively small weight-percentage of total excipients. This permits the tablets to contain/deliver a pharmaceutically effective amount of sodium oxybate in each tablet with a delivery profile similar to that of the liquid form. The tablets are bioequivalent to the liquid form. See U.S. Pat. Nos. 8,771,735 and 8,778,398. Other embodiments provide controlled release dosage forms for delivery of GHB or salt(s) thereof. The controlled release dosage forms may incorporate both controlled release and immediate release formulations in a single unit dosage form. See U.S. Publication No. 2012/0076865. Another embodiment includes the use of both immediate release and controlled release forms mixed together or one after the other. In one embodiment the immediate release portion could be between 10-50%, or 20-30% and the controlled release portion comprising the remaining amount. In some embodiments the amounts of the different salts can be different in each of the immediate or controlled release portions.

Additionally, any excipient, salt, acid, pH-mediating, adjusting or buffering compound or agent, flavoring, solution, solvent, dispersion, glycerol, glycol, oil, antibacterial and antifungal agents, antibiotics and antihistamines, binders, disintegrating agents, lubricants, sweetening agents, or any other additive or ingredient from those enumerated above or in the examples, or in any pharmaceutically acceptable composition or carrier described herein, or as would be known by one of skill in the art, is contemplated for use in aqueous mediums or solid forms of the pharmaceutical compositions disclosed herein. One or more of these compositions may be packaged with GHB or salt(s) thereof, or packaged separately from GHB or salt(s) thereof prior to consumption. If packaged separately, useful pharmaceutical compositions may be obtained by mixing GHB or salt(s) thereof with the other components with an aqueous medium prior to consumption. Such components may be packaged in a kit, described below.

Also provided herein are therapeutic kits comprising GHB, or a salt or mixture of salts of GHB, as disclosed herein. Such kits will generally contain, in suitable container, a pharmaceutically acceptable formulation of the GHB or salt(s) thereof. The kit may have a single container, or it may have distinct container for each component, or distinct container for various combinations of components.

When the components of the kit are provided in one or more liquid formulations, the liquid formulation is an aqueous medium, with a sterile aqueous solution being particularly preferred. The pharmaceutical compositions may also be formulated into a syringeable composition. In which case, the container means may itself be a syringe, pipette, vial, ampule or other such like apparatus, from which the formulation may be applied to an infected area of the body, injected into an animal, or even applied to and mixed with the other components of the kit.

However, the components of the kit may be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, pouch syringe or other container means, into which the formulation or components thereof are placed, preferably, suitably allocated. The kits may also comprise a second container means for containing a sterile, pharmaceutically acceptable buffer or other diluent.

The kits will also typically include a means for containing the vials in close confinement for commercial sale, such as, e.g., injection or blow-molded plastic containers into which the desired vials are retained.

In certain embodiments, the kits contain one or more bottles of liquid formulation comprising GHB or salt(s) thereof, two dosing cups with child-resistant caps, a liquid measuring device and a medication guide.

In certain embodiments, the kits contain two different GHB formulations in separate bottles. In certain embodiments, the kits contain two bottles of liquid formulation comprising GHB or salt(s) thereof, wherein two different formulations are provided in at least two separate bottles. In certain embodiments, the kits contain two or more bottles of liquid formulation comprising GHB or salt(s) thereof, wherein two different formulations are provided in at least two separate bottles, and wherein also provided are two dosing cups with child-resistant caps, one or more liquid measuring device and a medication guide. Preferably, the two different formulations are a first-dose formulation comprising an aqueous solution, the aqueous solution is a mixture of two or more GHB salts, the mixture comprising less than 50% Na.GHB, and further comprising one or more salts selected from K.GHB, Ca.(GHB)$_2$, and Mg.(GHB)$_2$, and the second-dose formulation comprising an aqueous solution comprising from 50% to about 80% of Na.GHB, and further comprising one or more salts selected from K.GHB, Ca.(GHB)$_2$, and Mg.(GHB)$_2$.

Irrespective of the number or type of containers, the kits may also comprise, or be packaged with, an instrument for assisting with the injection/administration or placement of the pharmaceutical composition within the body of an animal. Such an instrument may be a drinking cup, syringe, pipette, or any such medically approved delivery vehicle. Where two more formulations are provided in the kit, optionally, one or more of the instruments or formulations can be color-matched or labeled to indicate which of the two doses are contained within it. Furthermore, the drug product containers can be differentiated by color, shape or other identifying features. The containers can be bound together (for example, by shrink wrapping) or assembled into the kit in such a way to minimize misplacement or discourage dispensing of one product for both dosings. Where two or more formulations are provided as granules or other rapidly dissolving dosage form, twin sachets with a perforated divider can facilitate dose preparation. These could be labeled, for example, as "1$^{st}$ dose" and "2$^{nd}$ dose".

Furthermore and to distinguish between prepared formulations prior to administration, one or both of the formulations can include a flavorant, odorant, or colorant to render it substantially different from the other. The additive may also be provided separately in the kit so that it can be added to the water either immediately before or after dispensing each formulation. Also, the administration devices for each dose may be distinguished based on a number of features such as color, shape, etc. so that that patient can easily administer each dose.

6.2.3 Methods of Treatment

All the pharmaceutical compositions and formulations provided herein can be used in all the methods provided herein. For example, the pharmaceutical compositions and formulations provided herein can be used in all the methods for treating all diseases, disorders or conditions provided herein. Thus, the pharmaceutical compositions and formulations provided herein are for use as a medicament. In certain embodiments, the pharmaceutical compositions and formulations provided herein are for use in a method for treating cataplexy or daytime sleepiness in a patient who has been diagnosed with narcolepsy. In certain embodiments, the pharmaceutical compositions and formulations provided herein are for use in a method for treating cataplexy or daytime sleepiness in a patient who has been diagnosed with narcolepsy. In certain embodiments, the pharmaceutical compositions and formulations provided herein are for use in a method for treating a disease or condition in a subject that is suitable to treatment by GHB, comprising administering a pharmaceutical composition or formulation disclosed herein.

The pharmaceutical compositions and formulations comprising mixed salts of GHB, disclosed herein, are also contemplated to be useful in the treatment of any of these disorders or conditions in patients. GHB has also been used alone as a narcotic in patients with terminal cancer. GHB has been used with other analgesics, neuroleptics, or with a subliminal barbiturate dose for use as an anesthesia. It is also contemplated that the pharmaceutical compositions and formulations disclosed herein may be used as a narcotic, hypnotic, or as a soporific. It is further contemplated that the pharmaceutical compositions and formulations comprising mixed salts of GHB, disclosed herein, may be used in combination with analgesics, neuroleptics or barbiturates for use as an anesthesia. See the methods described at the end of U.S. Pat. No. 6,472,431.

The pharmaceutical compositions and formulations comprising mixed salts of GHB, disclosed herein, may be prepared and administered by any of the means described herein, particularly those described in the section "Formulations" and the examples, or by any means as would be known to those of skill in the art.

Accordingly, in certain aspects, are methods of treatment comprising administration to a patient of the pharmaceutical compositions or formulations comprising mixed salts GHB disclosed herein.

In certain embodiments, the pharmaceutical compositions or formulations comprising mixed salts of GHB, disclosed herein, are useful in the treatment of cataplexy or daytime sleepiness in a patient who has been diagnosed with narcolepsy.

In certain embodiments, the pharmaceutical compositions or formulations comprising mixed salts of GHB, disclosed herein, are useful in the treatment of conditions responsive to GHB, for example, sleep disorders such as apnea, sleep time disturbances, narcolepsy, cataplexy, excessive daytime sleepiness (EDS), sleep paralysis, hypnagogic hallucination, sleep arousal, insomnia, and nocturnal myoclonus.

Accordingly, in certain embodiments, provided herein is a method for treating a disease or condition in a subject that is suitable to treatment by GHB, comprising administering a pharmaceutical composition or formulation disclosed herein.

In certain embodiments, also provided herein is a method of treating a disease or condition that is suitable for treatment with GHB wherein the method comprises administering to a patient a pharmaceutical composition comprising from 50% to about 80% of Na.GHB, wherein the pharmaceutical composition is in an oral dosage form and wherein administration of the pharmaceutical composition produces a GHB Cmax which is bioequivalent to the Cmax of Na.GHB. In certain embodiments, the pharmaceutical composition does not comprise a substantial amount of Mg.$(GHB)_2$ or Ca.$(GHB)_2$. In certain embodiments, the disease or condition is selected from the group consisting of sleeping disorders, drug abuse, alcohol and opiate withdrawal, a reduced level of growth hormone, anxiety, analgesia, neurological disorders (e.g., Parkinson's Disease and depression), endocrine disturbances, hypoxia or anoxia of tissues (such as from stroke or myocardial infarction), or an increased level of intracranial pressure. In preferred embodiments, the disease is cataplexy and/or narcolepsy. In certain embodiments, the disease or condition is selected from the group consisting of fibromyalgia and sleep disorders such as apnea, sleep time disturbances, narcolepsy, cataplexy, excessive daytime sleepiness (EDS), sleep paralysis, hypnagogic hallucination, sleep arousal, insomnia, and nocturnal myoclonus.

In certain embodiments, the mixture of salts which from about 50% to about 80% of Na.GHB further comprises one or more salts selected from the group consisting of K.GHB and Ca.$(GHB)_2$.

In certain embodiments, also provided herein is a method of treating a disease or condition that is suitable for treatment with GHB wherein the method comprises administering to a patient a pharmaceutical composition of GHB comprising less than 100 mL of an aqueous solution, wherein the aqueous solution comprises a mixture of two or more salts of GHB, the mixture comprising between 40% and 50% Na.GHB, and further comprising one or more salts selected from K.GHB, Ca.$(GHB)_2$, and Mg.$(GHB)_2$. In certain embodiments, the disease is cataplexy and/or narcolepsy.

In certain embodiments, when administered to a patient, the pharmaceutical composition produces a GHB Cmax which is within 10% of the Cmax of Na.GHB. In certain embodiments, the Cmax is within 10% of the Cmax of a pharmaceutical composition comprising about the same amount of 100% Na.GHB when administered to a patient. In certain embodiments, when administered to a patient, the pharmaceutical composition produces a GHB Cmax that is bioequivalent to the Cmax of Na.GHB. In certain embodiments, the pharmaceutical composition is bioequivalent to a pharmaceutical composition comprising about 100% Na.GHB when administered to a patient. In certain embodiments, the AUC is within 10% of the AUC of a pharmaceutical composition comprising about the same amount of 100% Na.GHB when administered to a patient. In certain embodiments, the pharmaceutical composition does not comprise a substantial amount of Mg.$(GHB)_2$ or Ca.$(GHB)_2$. In certain embodiments, the disease or condition is selected from the group consisting of sleeping disorders, drug abuse, alcohol and opiate withdrawal, a reduced level of growth hormone, anxiety, analgesia, neurological disorders (e.g., Parkinson's Disease and depression), endocrine disturbances, hypoxia or anoxia of tissues (such as from stroke or myocardial infarction), or an increased level of intracranial pressure. In preferred embodiments, the disease is cataplexy and/or narcolepsy. In certain embodiments, the disease or condition is selected from the group consisting of fibromyalgia and sleep disorders such as apnea, sleep time disturbances, narcolepsy, cataplexy, excessive daytime sleepiness (EDS), sleep paralysis, hypnagogic hallucination, sleep arousal, insomnia, and nocturnal myoclonus.

In certain embodiments, the methods of treatment comprising administration of the pharmaceutical compositions or formulations comprising mixed salts GHB disclosed herein.

In certain embodiments, the method comprises oral administration of the pharmaceutical compositions or formulations comprising mixed salts GHB, disclosed herein, in a multiple dosage regimen.

In certain embodiments, the multiple dosage regimen comprises one or more steps, as follows: (i) diluting an aqueous solution comprising about 409 mg/mL of gamma-hydroxybutyrate (GHB) with an aqueous medium to provide a first dose of the mixture of salts; (ii) diluting an aqueous solution comprising about 409 mg/mL of GHB with an aqueous medium to provide a second dose of the mixture of salts; (iii) orally administering to a patient having narcolepsy the first dose; and (iv) orally administering to the patient having narcolepsy the second dose within 2.5 to 4 hours following the first dose. The first and/or second doses can be administered according to the instructions on the label as appropriate.

In certain embodiments, two nightly doses of GHB or a salt there are administered to the patient.

In certain embodiments, the first dose of GHB salts is a pharmaceutical composition of GHB comprising an aqueous solution of a mixture of two or more GHB salts, the mixture comprising less than 40% Na.GHB, and further comprising one, two, three or more salts selected from K.GHB, Ca.$(GHB)_2$, and Mg.$(GHB)_2$, and wherein the first dose is administered within 4 hours of eating and produces a GHB Cmax which is less than the Cmax of Na.GHB; and the second dose of GHB salts is a pharmaceutical composition of GHB comprising a mixture of two or more GHB salts, the mixture comprising at least 50% of Na.GHB, and further comprising one or more salts selected from K.GHB, Ca.$(GHB)_2$, and Mg.$(GHB)_2$, and wherein the second dose produces a GHB Cmax which is substantially equivalent to the Cmax of Na.GHB. In certain embodiments, the multiple dosage regimen comprises one or more steps, as follows: (i) diluting an aqueous solution comprising a mixture of two or more GHB salts, the mixture comprising 0% to 40% Na.GHB, and further comprising one or more salts selected from K.GHB, Ca.$(GHB)_2$, and Mg.$(GHB)_2$, with an aqueous medium to provide a first dose of GHB salts; (ii) diluting an aqueous solution comprising a mixture of two or more GHB salts, the mixture comprising from about 50% to about 80% of Na.GHB, and further comprising one or more salts selected from K.GHB, Ca.(GHB)$_2$, and Mg.(GHB)$_2$, to provide a second dose of GHB salts; (iii) orally administering the first dose to a patient suitable for treatment with GHB; and (iv) orally administering the second dose to the patient within 2.5 to 4 hours following the first dose. In preferred embodiments, the patient is suitable for treatment with GHB has cataplexy or narcolepsy.

In certain embodiments, the first dose comprises a pharmaceutical composition comprising less than 40% Na.GHB and at least two other GHB salts selected from the group of K.GHB, Ca.(GHB)$_2$, and Mg.(GHB)$_2$. In certain embodiments, the first dose is administered within 4 hours of eating. In certain embodiments, the mixture further comprises two or more salts selected from the group consisting of K.GHB, Ca.(GHB)$_2$, and Mg. (GHB)$_2$.

In certain embodiments, the disease or condition is selected from the group consisting of a sleeping disorder, drug abuse, alcohol and opiate withdrawal, a reduced level of growth hormone, anxiety, analgesia, a neurological disorder, an endocrine disturbance, hypoxia or anoxia of tissues, and an increased level of intracranial pressure.

In certain embodiments, the first dose of GHB salts is a pharmaceutical composition of GHB comprising an aqueous solution of less than 100 mL, the aqueous solution comprises a mixture of three GHB salts, the mixture comprising less than 50% Na.GHB, and further comprising one or more salts selected from between 10-60% K.GHB, Ca.(GHB)$_2$, and Mg.(GHB)$_2$, and wherein the first dose is administered within 4 hours of eating and produces a GHB Cmax which is less than the Cmax of Na.GHB.

In certain embodiments, the second dose of GHB salts is a pharmaceutical composition of GHB comprising an aqueous solution, the aqueous solution comprising from 50% to about 80% of Na.GHB, and from between 10-60% K.GHB, Ca.(GHB)$_2$, and Mg.(GHB)$_2$, and wherein administration of the second dose produces a GHB Cmax which is substantially bioequivalent to the Cmax of Na.GHB. In certain embodiments, the second dose of GHB salts is a pharmaceutical composition of GHB comprising an aqueous solution which comprises a mixture from 50% to about 80% of Na.GHB, and wherein administration of the second dose produces a GHB Cmax which is substantially bioequivalent to a composition comprising Na.GHB.

In certain embodiments, 4.5 and 9 grams/day are administered to the patient in two divided doses.

In certain embodiments, 6 and 8 grams/day are administered to the patient in two divided doses.

In certain embodiments, the disease or condition is selected from the group consisting of sleeping disorders, drug abuse, alcohol and opiate withdrawal, a reduced level of growth hormone, anxiety, analgesia, neurological disorders (e.g., Parkinson's Disease and depression), endocrine disturbances, hypoxia or anoxia of tissues (such as from stroke or myocardial infarction), or an increased level of intracranial pressure.

It will be understood, however, that the specific dose level and frequency of dosage for any particular patient may be varied and will depend upon a variety of factors including: the metabolic stability and length of action, the age, body weight, general health, sex, diet, mode and time of administration, rate of excretion, drug combination, the severity of the particular condition, and the host undergoing therapy.

6.2.4 Methods of Making

In certain aspects, provided herein are some exemplary methods of making the compositions or formulations comprising mixed salts GHB disclosed herein. Several different methods of making have been reported in the literature (see, e.g., U.S. Pat. Nos. 4,393,236; 4,983,632; 6,472,431; 8,461,203; 8,591,922; 8,901,173; and 9,132,107; and U.S. Publication No. 2016/0058720, each of which is incorporated by reference in its entirety; see also Ferris and Went, 2012, *Forensic Science International* 216: 158-162). Those skilled in the art will recognize that these methods can be incorporated in the making of the compositions or formulations comprising mixed salts GHB disclosed herein. Other methods will be known to those of skill in the art.

In certain embodiments, mixtures of GHB salts can be made by direct reaction of GBL with an aqueous mixture of one of more of the following bases: sodium hydroxide, potassium hydroxide, calcium hydroxide, and magnesium hydroxide. After reaction the mixture may then be filtered under mild vacuum.

In certain embodiments, a solvent, such as water, is used to dissolve the GHB salt mixture to a desired concentration, for example, by adjusting the amount of water in the mixture.

In certain embodiments, the concentration of a GHB salt solution is adjusted by concentrating the mixture using standard methods, such as evaporators, reverse osmosis, and similar techniques known to those skilled in the art.

In certain embodiments, the method of making comprises reacting gamma-butyrolactone (GBL) with one or more bases selected from the group consisting of sodium hydroxide, potassium hydroxide, magnesium hydroxide, and calcium hydroxide.

In other embodiments, the method of making comprises, for example, reacting GBL with one or more of sodium carbonate, potassium carbonate, or magnesium carbonate to provide the sodium, potassium, and magnesium oxybate (Na.GHB, K.GHB, and Mg.(GHB)$_2$) mixture. Such embodiments are particularly suitable to avoid precipitation of calcium carbonate when carbonate salts of sodium, potassium, and/or magnesium are employed.

In still other embodiments, a solution of calcium oxybate can be transformed to a mixture of oxybate salts by exchanging with a mixture of cation exchange resins loaded with the desired cations. Alternatively, a solution of calcium oxybate can be transformed to a mixture of oxybate salts by precipitation with a mixture of acid salts of other cations when the calcium salt is practically insoluble. After filtration or other means of removing the precipitated calcium salt or the exchanged cation exchange resin, the mixed oxybate salt solution is obtained.

In other embodiments, a mixture of cations associated with oxybate may include a proton. This can be achieved in similar fashion as cation exchange or displacement precipitation described above, with the exception that a H-form cation exchange resin or the free acid or partially neutralized salt of the precipitating anion is employed, respectively. Ideally to promote chemical stability, such embodiments should be produced in solid form and suspended or dissolved in water upon administration. In yet another embodiment, the undissolved solid (exchanged cationic resin or precipitated salt) can be ingested with the dose provided neither dissolves appreciably in the GI tract.

In certain embodiments, the reaction is carried out in a single vessel. For example, a mixture of Na.GHB, K.GHB, Mg.(GHB)$_2$, and Ca.(GHB)$_2$ may be made by direct addition of GBL to in a single vessel containing an aqueous mixture of sodium hydroxide, potassium hydroxide, magnesium hydroxide, and calcium hydroxide.

In certain embodiments, the reaction is carried out in multiple vessels and the product is subsequently combined. For example, Ca.(GHB)$_2$ may be made by direct addition of GBL to aqueous sodium hydroxide, and the product combined with Mg.(GHB)$_2$.

In certain embodiments, the methods of making include methods of making the pharmaceutical compositions and formulations disclosed herein.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the and scope of the invention.

7. EXAMPLES

Example 1: Synthesis of Mixed Oxybate Solutions

The following synthetic examples provide exemplary syntheses of mixture of oxybate salts. Alternate methods of synthesizing mixtures of oxybate salts, including methods of synthesizing additional salts of oxybate are described below; still other alternate synthetic methods will be apparent to those skilled in the art. See also U.S. Pat. Nos. 8,461,203; 8,591,922; 8,901,173; and 9,132,107; and U.S. Publication No. 2016/0058720; each of which is incorporated by reference in its entirety.

Mixed oxybate salt solutions can be made conveniently by at least two methods. When multiple different formulations are desired, one of skill in the art can mix solutions of individual salts having the same molar oxybate concentration to arrive at the desired cation blend. On the other hand, for commercial implementation or single-batch manufacturing one can perform a one-pot reaction with GBL and the two or more bases in the desired cationic proportions. Both methods are described below.

Example calculations of molar equivalents and % wt/wt for salt mixtures are also shown below Table 1.

TABLE 1

Example Calculations

| Base | Base MW | Purity | Grams Amount | Base mMols | Stoich. Ratio | Base mEQ | % molar equiv GHB | Salt | Salt MW | Salt mass grams | Salt wt/wt % | Conc mg/mL |
|---|---|---|---|---|---|---|---|---|---|---|---|---|
| NaOH | 40.00 | 98.50% | 1.398 | 34.43 | 1 | 34.43 | 8.5% | Na•GHB | 126.09 | 4.34 | 8.5% | 42.61 |
| KOH | 56.11 | 86.72% | 7.337 | 113.40 | 1 | 113.40 | 28.0% | K•GHB | 142.20 | 16.12 | 31.4% | 158.29 |
| Ca(OH)$_2$ | 74.10 | 99.00% | 6.268 | 83.74 | 2 | 167.49 | 41.4% | Ca•(GHB)$_2$ | 246.27 | 20.62 | 40.2% | 202.46 |
| Mg(OH)$_2$ | 58.32 | 99.50% | 2.611 | 44.55 | 2 | 89.09 | 22.0% | Mg•(GHB)$_2$ | 230.50 | 10.27 | 20.0% | 100.80 |
| Total | | | 17.614 | 276.11 | | 404.40 | 100.0% | | | 51.36 | 100.0% | 504.17 |

| | |
|---|---|
| Base | Each of four bases used in this example |
| Base MW | Molecular weight of the base |
| Purity | Purity provided by manufacturer. It is assumed that impurities are non-reactive. |
| Gram Amount | Amount, in grams, of each base charged to the reaction |
| Base mMols | Corresponding amount, in millimoles, of pure base (that is, Purity × Gram-Amount × 1000/Base-MW) |
| Stoichiometry Ratio | The number of GHB moles reacted with each mole of base |
| Base mEQ | Base equivalents for reaction with GHB (that is, Base-mMols × Stiochiometry-Ratio). This is also the Oxybate or GHB equivalents value. |
| % molar equiv GHB | Molar composition of salts expressed as Percent of Oxybate Equivalents |
| Salt | The oxybate salt species |
| Salt MW | Molecular weight of the oxybate salt |
| Salt-mass-grams | Mass of salt produced by reaction (that is, Base-mMols × Salt-MW/1000) |
| Salt wt/wt % | Normalized weight percent |
| Conc. (mg/ml) | Concentration in mg/ml equivalent to a 3.97M Na-GHB solution (500 mg/ml sodium oxybate). That is, 3.97 × (% equiv-GHB) × (Salt-MW)/(Stoich. Ratio) |

Example 1.1: Manufacturing Mixed Salts Solutions

Four individual oxybate salt solutions at equal oxybate strength (409 mg/mL) were made as follows:

Magnesium oxybate (Mg.(GHB)$_2$) solution was made by combining 124.6 g water and 20.36 g magnesium hydroxide in a magnetically-stirred 250 mL square glass bottle. 58.04 g of GBL was then added to the base suspension and then heated up to 80° C. with stirring. After 4 hours, a pH verification indicated completion of reaction (pH 8.5). Water was added to compensate for evaporation. The reaction mixture was then centrifuged, and supernatant filtered through 0.45µ. PVDF Stericup under vacuum. The pH of filtrate was 8.1. Yield: 177.4 g solution. Assay (HPLC-UV): 100.1%

Potassium oxybate (K.GHB) solution was made by adding 60.10 g potassium hydroxide to 144.01 g water in a magnetically-stirred 250 mL square glass bottle. After complete dissolution, 78.52 g GBL was weighed into a separate glass beaker. Approximately half the GBL was added initially with instant reaction, and then the solution was cooled in ice water to approximately 30° C. The remainder of the GBL was then added with stirring, and the solution maintained at 60° C. for 2.5 hours. The pH was 13.5. The pH was then adjusted to 8.1 by adding 10% HCl solution. Water was added to restore the initial reaction mass. The solution was then filtered through 0.45µ. PVDF Stericup under vacuum. Yield: 281.8 g solution. Assay (HPLC-UV): 98.6%.

Calcium oxybate (Ca.(GHB)$_2$) solution was made by combining 210.5 g water and 45.41 g calcium hydroxide in a magnetically stirred 500 mL square glass bottle. Next, 102.41 g GBL was added slowly while stirring, and then the reaction was maintained at 80° C. on a temperature-controlled hotplate (surface set point 183° C.). After 2 hours, the mixture was cooled and water was added to compensate for evaporation. The solution was centrifuged, and supernatant was then filtered through 0.45μ. PVDF Stericup under vacuum. The initial pH of filtrate was 10.5, and was adjusted to 7.9 by addition of 10% HCl solution. Yield: 328.6 g solution. Assay (HPLC-UV): 99.0%

Sodium oxybate (Na.GHB) solution was made by adding 46.6 g sodium hydroxide to 200.1 g water in a magnetically stirred 500 mL square glass bottle. 99.00 g GBL was weighed into a separate beaker. After complete dissolution of the sodium hydroxide, about half of the GBL was added to the reaction mixture causing it to heat. After cooling to about 30° C. in ice water, the remaining GBL was added and then allowed to react with stirring on a hotplate at 60° C. for 2 hours. The pH after reaction was 12.36, and was adjusted to 8.13 by addition of 10% HCl solution. Water was added to restore the initial reaction mass. The solution was then filtered through a 0.45μ. PVDF Stericup under vacuum. Yield: 340.3 g. Assay (HPLC-UV): 100.6%.

For each desired oxybate salt mixture below, the individual solutions were blended volumetrically with an oral dosing syringe into a 250 mL glass beaker with stirring. The blend order, where applicable, was sodium, potassium, calcium, and then magnesium oxybate. 178 mg of sucralose was then added and dissolved. The target cation blends (in equivalents) and volumes of individual solutions used are shown in Table 2 below.

TABLE 2

Target Cation Blends and Volumes of Exemplary Solutions

| | % equivalents | | | | Volume (mL) of oxybate solution (#1-#4 above) for total batch 150 mL | | | | Assay |
|---|---|---|---|---|---|---|---|---|---|
| Solution | Na | K | Ca | Mg | Na (#4) | K (#2) | Ca (#3) | Mg (#1) | % Label |
| 507-A | 33 | 34 | 33 | 0 | 49.5 | 51.0 | 49.5 | 0 | 98.9 |
| 507-G | 23.3 | 19.2 | 40 | 17.5 | 35.0 | 28.8 | 60.0 | 26.3 | 99.2 |
| 507-C | 33 | 0 | 48 | 19 | 49.5 | 0 | 72.0 | 28.5 | 100.0 |
| 507-D | 50 | 34 | 16 | 0 | 75.0 | 51.0 | 24.0 | 0 | 98.8 |

Example 1.2: Direct, One-Pot Reaction Method to Achieve Various Mixtures

To achieve any combination of oxybate salts, the stoichiometry calculations are adjusted to reflect (a) the strength of individual bases and (b) the use of an excess for the weakest base (calcium or magnesium). The strength of bases used in the Example above were 99.7% (NaOH), 86.0% (KOH), 99.0% (Ca.(OH)$_2$), and 98.5% (Mg.(OH)$_2$). A 1% excess is applied as the weakest divalent base present (calcium or magnesium, in that order of precedence). A larger or smaller excess may be warranted, depending on the level of confidence in the assay values or repeatability of dispensing to the process. A larger excess will increase confidence in completing the reaction, but incur more filtration load. A smaller excess threatens to inadequately complete the reaction, resulting in higher than desired GBL levels.

To make 150 mL batches roughly equivalent in composition to those of Example 1.1, the stoichiometry is as shown in Table 3 below.

TABLE 3

Stoichiometry of Bases used for Exemplary Solutions

| | grams base required | | | | Excess | | GBL | Water | Total |
|---|---|---|---|---|---|---|---|---|---|
| Solution | NaOH | KOH | Ca(OH)$_2$ | Mg(OH)$_2$ | As base | grams | grams | grams | grams |
| 507-A | 7.88 | 13.21 | 7.35 | 0.00 | Ca(OH)$_2$ | 0.22 | 51.27 | 98.56 | 178.5 |
| 507-G | 5.57 | 7.46 | 8.91 | 3.12 | Mg(OH)$_2$ | 0.17 | 51.27 | 102.00 | 178.5 |
| 507-C | 7.88 | 0.00 | 10.70 | 3.38 | Mg(OH)$_2$ | 0.17 | 51.27 | 105.09 | 178.5 |
| 507-D | 11.95 | 13.21 | 3.57 | 0.00 | Ca(OH)$_2$ | 0.22 | 51.27 | 98.29 | 178.5 |

The water is weighed into a tared 250 mL beaker with spinbar. Next, bases are weighed and added in order of sodium, potassium, calcium, and magnesium as applicable. After sodium or potassium hydroxide is added, the mixture is stirred until complete dissolution is observed. The required excess is added at the same time as the respective base is charged. Next, 51.27 g of GBL is added slowly while monitoring temperature and with stirring. If the temperature exceeds about 80° C., then GBL addition is slowed until the temperature cools to about 60° C. After GBL addition is complete, the setup is moved to a 60° C. environmental chamber to complete the reaction. (Alternatively, a temperature-controlled hotplate can be employed.) Sodium and potassium hydroxide react almost instantly with GBL. Ca.(OH)$_2$ requires about 1 h to react at 60° C., and Mg.(OH)$_2$ requires about 3 h at 80° C. or overnight (12 h) at 60° C. Therefore, mixtures lacking Mg.(OH)$_2$ (507-A and 507-D) are held at 60° C. for about 1 h. Mixtures 507-G and 507-C are held at 60° C. overnight or 80° C. for 3 h.

After reaction, water is added to compensate for evaporation and restore the original reaction mass (178.5 g net). The reaction mixtures are then centrifuged followed by vacuum filtration through a 0.45μ. PVDF Stericup. Finally, the pH is adjusted with 10% HCl solution, as needed, to a value of 8.0. For mixtures containing magnesium, no adjustment is required if the pH is below 9. Finally, 0.18 g of sucralose is added and dissolved into the solution.

Example 2: Pharmacokinetic Testing of Formulations

This Example provides protocols and results for bioequivalence testing of the formulations disclosed herein. Four sets of bioequivalence testing were performed with various mixed salt formulations compared with Xyrem® as the reference. Unless stated otherwise, this and subsequent examples have oxybate salt concentrations stated in a "molar equivalent percent" basis. Furthermore, in the tables and figures where applicable:
- "Treatment" refers to the formulation and the dosing regimen (fed or fasted), for which various formulations were tested at a dose equivalent to 4.5 g sodium oxybate.
- "N" refers to the number of subjects for which evaluable results were obtained
- "Vol" refers to the volume of administration (mL) given with the 9 mL dose of drug product
- "Cmax" refers to the average of the maximum plasma concentration (in oxybate mg/L or ug/mL) achieved in individual patients
- "Cmax Ratio" refers to the ratio of Cmax value compared to that of fasted state Xyrem® and expressed as a percentage
- "AUC" refers to the area under the curve of plasma vs time, either the last time point where the concentration was above the limit of quantitation or projected out to infinite time and expressed in units of h*mg/L.
- "AUC ratio" refers to the ratio of AUC to that of fasted state Xyrem® and expressed as percentage
- "Na", "K", "Ca", and "Mg" refer to the cation content of the formulation given, in Molar Equivalent %, of sodium, potassium, calcium, and magnesium, respectively.

Example 2.1: Testing of Formulation "O"

Formulation "O" was manufactured as (equivalent %) 8% sodium, 23% potassium, 48% calcium, and 21% magnesium oxybate at 409 mg/mL mixed salt concentration or 409 mg/mL oxybate. The four bases were suspended or dissolved in water, then gamma butyrolactone was added and the reaction mixture was held at 80° C. for about 3 hours. Subsequently, mixture was cooled and then depth filtered, carbon filtered, and then flowed through a polishing filter. Finally, sucralose was added to a level of 0.1% w/v in the final solution.

Formulation "O" was tested for bioequivalence relative to Xyrem® (Formulation "X", commercial sodium oxybate solution of the same molar concentration and comparable pH as "O") and in the fasted as well as fed state. The study was compliant with the FDA guidance for food effect studies ("Guidance for Industry: Food-Effect bioavailability and Fed Bioequivalence Studies", FDA December 2002), incorporated herein by reference in its entirety. In both fasted and fed treatments, the Guidance indicates that the drug product should be administered with 240 mL of water. Thirty-six patients were recruited and 34 patients completed successfully. The results are shown in FIG. 1 and in Table 4 below.

TABLE 4

Conditions and Results in Study 13-010 Using 240 mL Liquid Volume

| Treatment | Number of Patients | Vol (mL) | Cmax (mg/L) | Cmax ratio | AUC (mg•h/L) | AUC ratio | % equivalent Na | K | Ca | Mg |
|---|---|---|---|---|---|---|---|---|---|---|
| O, fasted | 34 | 240 | 102.3 | 76% | 238.7 | 89% | 8 | 23 | 48 | 21 |
| O, fed | 36 | 240 | 77.7 | 58% | 216.0 | 81% | 8 | 23 | 48 | 21 |
| X, fasted | 32 | 240 | 134.6 | 100% | 268.1 | 100% | 100 | 0 | 0 | 0 |
| X, fed | 36 | 240 | 84.9 | 63% | 233.0 | 87% | 100 | 0 | 0 | 0 |

Example 2.2: Testing of Blends of Xyrem® and Formulation "O"

As an extension to the study described in Example 2.1, the same formulation "O" and Xyrem® reference were tested in two different proportions to determine whether bioequivalence could be achieved with the same proportion of the three non-sodium cations but with higher sodium content. New patients were recruited for the single dose crossover study, but the study was otherwise done in a manner comparable to Example 2.1 except fewer patients were evaluated. The results are shown in FIG. 2 and Table 5 as expressed in mean values. Bioequivalence was not achieved even at 49% sodium (the confidence interval for that formulation was between 73.8-97.5%).

TABLE 5

Conditions and Results in Study 13-010 Part 2 using 240 mL Liquid Volume

| Treatment | Number of Patients | Vol (mL) | Cmax (mg/L) | Cmax ratio | AUC (mg•h/L) | AUC ratio | % equivalent Na | K | Ca | Mg |
|---|---|---|---|---|---|---|---|---|---|---|
| 2.5 g O + 2.0 g X, fasted | 21 | 240 | 109.4 | 84% | 241.3 | 96% | 49 | 13 | 27 | 12 |
| 3.75 g O + 0.75 g X, fasted | 19 | 240 | 98.18 | 75% | 228.4 | 91% | 23 | 19 | 40 | 18 |
| X, fasted | 17 | 240 | 130.2 | 100% | 251.4 | 100% | 100 | | | |

Example 2.3: Testing of Alternative Cationic Blends

To test for negative effects of certain cations and also to investigate other four-cation blends, the formulations of Example 1.1 were tested in a crossover fasted state bioequivalence study involving 35 patients. In contrast to the preceding two examples, the volume of administration was reduced to 60 mL. The results are shown in FIG. 3 and Table 6.

Surprisingly, as shown in FIG. 3 and Table 6, Formulation 507-D with 50% sodium met the bioequivalence criteria, as it had a Cmax ratio of 92% and nearly identical average plasma profile compared to Xyrem®. In contrast, Formulations 507-A and 507-C, both with 33% sodium but differing by exclusion of either potassium or magnesium, had nearly identical and lower Cmax values (78% and 76%, respectively), and therefore did not meet the bioequivalence criteria.

TABLE 6

Conditions and Results in Study 15-008 using 60 mL Liquid Volume, n = 35 patients

| Treatment | Vol (mL) | Cmax (mg/L) | Cmax ratio | AUC (mg•h/L) | AUC ratio | % equivalent Na | K | Ca | Mg |
|---|---|---|---|---|---|---|---|---|---|
| 507-A, fasted (no Mg) | 60 | 102.2 | 77% | 241 | 85% | 33 | 34 | 33 | 0 |
| 507-C, fasted (no K) | 60 | 101.0 | 77% | 252 | 89% | 33 | 0 | 48 | 19 |
| 507-D, fasted (higher Na, No Mg) | 60 | 120.8 | 92% | 257 | 90% | 50 | 34 | 16 | 0 |
| 507-G (3.75 g O + 0.75 g X, fasted | 60 | 95.6 | 72% | 246 | 87% | 23 | 19 | 40 | 18 |
| X, fasted | 60 | 131.9 | 100% | 284 | 100% | 100 | 0 | 0 | 0 |

Example 2.4: Testing Effect of Dilution Volume

Formulation 507-D having 50% sodium and tested at 60 mL volume was bioequivalent to Xyrem®, yet the four-cation blend of Example 2.2 having 49% sodium and tested at 240 mL volume was not bioequivalent. The difference between the two results is statistically significant and meaningful. To determine whether or how the volume of administration affects behavior of formulations, Formulation "O" was tested and compared to Xyrem® in three treatments fasted with 60 mL volume given, fasted with 240 mL volume, and fed with 60 mL volume. Thus, six treatments were administered in a crossover fashion involving 33 patients in a food effect bioequivalence study. The results are shown in FIG. 4 and Table 7.

There is little difference in the primary PK parameters (Cmax and AUC) as a result of volume of administration; however, there appears to be a difference in the mean plasma profile for Xyrem® at the two volumes when given fasted (FIG. 4).

TABLE 7

Results of Study JZP258-101, n = 33 patients

| Treatment | Vol (mL) | Cmax (mg/L) | Cmax ratio | AUC (mg•h/L) | AUC ratio | % equivalent Na | K | Ca | Mg |
|---|---|---|---|---|---|---|---|---|---|
| O, fasted | 60 | 93.0 | 77% | 238 | 95% | 8 | 23 | 48 | 21 |
| O, fasted | 240 | 92.7 | 74% | 233 | 90% | 8 | 23 | 48 | 21 |
| O, fed | 60 | 63.0 | 52% | 202 | 80% | 8 | 23 | 48 | 21 |
| X, fasted | 60 | 120.5 | 100% | 251 | 100% | 100 | 0 | 0 | 0 |
| X, fasted | 240 | 125.9 | 100% | 258 | 100% | 100 | 0 | 0 | 0 |
| X, fed | 60 | 68.6 | 57% | 206 | 82% | 100 | 0 | 0 | 0 |

Although the effect of dilution volume on food effect was not directly challenged in a single study, comparison of data from two crossover studies is possible for formulations "O" and Xyrem®. Table 8 shows the comparison of data from study JZP258-101 for 60 mL dilution volume and from study 13-010 Part 1 for 240 mL dilution volume. The results indicate that formulation "O" has a reduced food effect compared to Xyrem® and that, in both cases, the higher dilution volume has a smaller food effect.

TABLE 8

Comparison of Food Effect at 60 mL and 240 mL dilution

| Treatment | Cmax (mg/L) | | AUC (mg · h/L) | |
|---|---|---|---|---|
| Volume | 60 mL | 240 mL | 60 mL | 240 mL |
| O, fasted | 93.0 | 102.3 | 238 | 239 |
| O, fed | 63.0 | 77.7 | 202 | 216 |
| Ratio of O, fed to O, fasted | 68% | 76% | 85% | 90% |
| X, fasted | 120.5 | 134.6 | 251 | 268 |
| X, fed | 68.6 | 84.9 | 206 | 233 |
| Ratio of X, fed to X, fasted | 57% | 63% | 82% | 87% |

In similar fashion, comparison of fasted data across studies can be done. FIG. 5A shows the Cmax ratio as a function of the percent of calcium in the formulation. FIG. 5B shows the Cmax ratio as a function of the percent of sodium in the formulation. The calcium model was arrived at by stepwise regression of main effect and interaction of calcium % and volume of administration using JMP software (SAS Institute). Volume of administration and its interaction were both dropped as insignificant terms. (An alternative model process employing calcium % and diluted concentration—which is volume-dependent—provided no better fit.) The result has significant lack of fit.

On the other hand, when sodium level and sodium diluted concentration (and interaction) are considered, a significantly better fit to results was obtained. All three terms were significant at 90% confidence or better, yet the main effect of diluted sodium concentration was least significant of the three). Sodium level and its interaction with diluted sodium concentration were highly significant, respectively). That model fit is shown in FIG. 5B.

Example 3: Expected Pharmacokinetics of Two Formulations Dosed 4 Hours Apart

The following proposed test treatment consists of administering formulation "O" of preceding examples and administering a second dose of formulation "507-D" 4 hours later. The reference treatment consists of Xyrem® given in the same fashion. Test and reference treatments have the same oxybate dose and are administered in 60 mL of water in the evening approximately two hours after dinner. Plasma is sampled at the same intervals as in preceding examples.

The outcome can be estimated by assuming additive contributions from each dose based on the single dose PK evaluations presented in preceding examples. The expected results are shown in FIG. 6 compared to those of the reference Xyrem® given under the same conditions.

Example 4: Microbial Challenge

This Example demonstrates that a mixed oxybate salt having low sodium displays acceptable resistance to microbial growth. A solution having, on a molar equivalents basis, 8% sodium, 23% potassium, 48% calcium, and 21% magnesium oxybate salts (Na.GHB, K.GHB, Mg.(GHB)$_2$, and Ca.(GHB)$_2$) with a pH value of 8 and a total concentration of 409 mg/mL oxybate salts was tested for antimicrobial effectiveness according to USP<51>. Individual samples were inoculated with each of five microorganisms and stored for 28 days at 20-25° C. At 7, 14, and 28 days microbial enumeration tests revealed effective reductions for all strains, as shown in Table 9 below.

TABLE 9

Microbial Effective
Test of 8% Na•GHB, 23% K•GHB,
48% Ca•(GHB)$_2$, and 21%
Mg•(GHB)$_2$ at 409 mg/mL
Log reduction in colony forming units/mL

| Organism | Day 7 | Day 14 | Day 28 |
| --- | --- | --- | --- |
| S. aureus | >5.2 | >5.2 | >5.2 |
| E. coli | >5.7 | >5.7 | >5.7 |
| P. aeruginosa | >5.8 | >5.8 | >5.8 |
| C. albicans | 3.0 | >5.6 | >5.6 |
| A. niger | 2.6 | 3.6 | >4.2 |

What is claimed is:

1. A method of reducing food effect due to administration of gamma-hydroxybutyrate (GHB) in a patient having cataplexy in narcolepsy or excessive daytime sleepiness in narcolepsy, comprising:
   orally administering to a patient in need thereof a pharmaceutically effective amount of a pharmaceutical composition of GHB in a unit dosage comprising at least one salt of GHB and a pharmaceutically acceptable carrier within four hours after eating;
   wherein the pharmaceutical composition of GHB has reduced food effect as measured by $C_{max}$ compared to an equal dose of immediate release liquid solution of Na.GHB, wherein the pharmaceutical composition comprises: about 5% to about 10% of Na.GHB; about 20% to about 25% of K.GHB; about 45% to about 50% of Ca.(GHB)$_2$; and about 20% to about 25% of Mg.(GHB)$_2$.

2. The method of claim 1, wherein the composition is administered with food, immediately after eating, up to 30 minutes after eating, or up to two hours after eating.

3. The method of claim 1, wherein the composition provides an AUC when administered within four hours after eating that is 80%-95% of the AUC when the composition is administered while fasting.

4. The method of claim 1, wherein the composition provides an AUC when administered within four hours after eating that is 85%-90% of the AUC when the composition is administered while fasting.

5. The method of claim 1, wherein the composition provides a $C_{max}$ when administered within four hours after eating that is 55%-80% of the $C_{max}$ when the composition is administered while fasting.

6. The method of claim 1, wherein the composition provides a $C_{max}$ when administered within four hours after eating that is 60%-75% of the $C_{max}$ when the composition is administered while fasting.

7. The method of claim 1, wherein the composition provides a $C_{max}$ that is less than the $C_{max}$ of an equal dose of immediate release liquid solution of Na.GHB administered in equally divided doses at least four hours after eating.

8. The method of claim 1, wherein the composition provides a $C_{max}$ that is less than the $C_{max}$ of an equal dose of immediate release liquid solution of Na.GHB administered in equally divided doses within four hours after eating.

9. The method of claim 1, wherein the composition provides a $C_{max}$ that is less than 60% the $C_{max}$ of an equal dose of immediate release liquid solution of Na.GHB administered in equally divided doses at least four hours after eating.

10. The method of claim 1, wherein the composition provides a change in $C_{max}$ when administered at least four hours after eating and within four hours after eating that is 10-60% less than the change in $C_{max}$ of an equal dose of immediate release liquid solution of Na.GHB when administered in equally divided doses at least four hours after eating and within four hours after eating.

11. The method of claim 1, wherein the pharmaceutical composition comprises 8% of Na.GHB; 23% of K.GHB; 48% of Ca.(GHB)$_2$; and 21% of Mg.(GHB)$_2$.

* * * * *

UNITED STATES PATENT AND TRADEMARK OFFICE
CERTIFICATE OF CORRECTION

PATENT NO. : 11,426,373 B2
APPLICATION NO. : 17/131418
DATED : August 30, 2022
INVENTOR(S) : Allphin et al.

Page 1 of 1

It is certified that error appears in the above-identified patent and that said Letters Patent is hereby corrected as shown below:

In the Claims

At Claim 1, Column 40, Line 9, please delete "Na.GHB" and replace with --Na•GHB--

At Claim 1, Column 40, Line 10, please delete "Na.GHB" and replace with --Na•GHB--

At Claim 1, Column 40, Line 11, please delete "K.GHB" and replace with --K•GHB--

At Claim 1, Column 40, Line 12, please delete "Ca.(GHB)$_2$" and replace with --Ca•(GHB)$_2$--

At Claim 1, Column 40, Line 13, please delete "Mg.(GHB)$_2$" and replace with --Mg•(GHB)$_2$--

At Claim 7, Column 40, Line 34, please delete "Na.GHB" and replace with --Na•GHB--

At Claim 8, Column 40, Line 38, please delete "Na.GHB" and replace with --Na•GHB--

At Claim 9, Column 40, Line 42, please delete "Na.GHB" and replace with --Na•GHB--

At Claim 10, Column 40, Line 49, please delete "Na.GHB" and replace with --Na•GHB--

At Claim 11, Column 40, Line 53, please delete "Na.GHB" and replace with --Na•GHB--

At Claim 11, Column 40, Line 53, please delete "K.GHB" and replace with --K•GHB--

At Claim 11, Column 40, Line 54, please delete "Ca.(GHB)$_2$" and replace with --Ca•(GHB)$_2$--

At Claim 11, Column 40, Line 54, please delete "Mg.(GHB)$_2$" and replace with --Mg•(GHB)$_2$--

Signed and Sealed this
Twenty-seventh Day of December, 2022

Katherine Kelly Vidal
*Director of the United States Patent and Trademark Office*